United States Patent
McDevitt et al.

(10) Patent No.: US 6,903,238 B2
(45) Date of Patent: Jun. 7, 2005

(54) SUBSTITUTED INDENONES AS ESTROGENIC AGENTS

(75) Inventors: Robert E. McDevitt, Somerset, NJ (US); Folake O. Adebi, Blackwood, NJ (US); Heather A. Harris, Phoenixville, PA (US); James C. Keith, Jr., Andover, MA (US); Leo M. Albert, Burlington, MA (US)

(73) Assignee: Wyeth, Madison, NJ (US)

( * ) Notice: Subject to any disclaimer, the term of this patent is extended or adjusted under 35 U.S.C. 154(b) by 240 days.

(21) Appl. No.: 10/316,446

(22) Filed: Dec. 11, 2002

(65) Prior Publication Data

US 2003/0166643 A1 Sep. 4, 2003

Related U.S. Application Data

(60) Provisional application No. 60/341,188, filed on Dec. 13, 2001.

(51) Int. Cl.$^7$ .................. C07C 49/115; A61K 31/12
(52) U.S. Cl. .................. 568/326; 568/330; 568/333; 514/680; 514/684
(58) Field of Search ............... 568/326, 330, 568/333; 514/680, 684

(56) References Cited

U.S. PATENT DOCUMENTS 5,998,402 A * 12/1999 Miller et al. ............... 514/183

OTHER PUBLICATIONS

Anstead et al. 2,3–Diarylindenes and 2,3–Diarylindenones: Synthesis, Molecular Structure, Photochemistry, Estrogen Receptor Binding Affinity, and Comparisons with Related Triarylethylenes. Journal of Medicinal Chemistry, 1988, vol. 31, p 1316–1326.*

* cited by examiner

Primary Examiner—James O. Wilson
Assistant Examiner—Sikarl A. Witherspoon
(74) Attorney, Agent, or Firm—Arnold S. Milowsky, Esq.; Cozen O'Connor

(57) ABSTRACT

This invention provides estrogen receptor modulators of formula I, having the structure

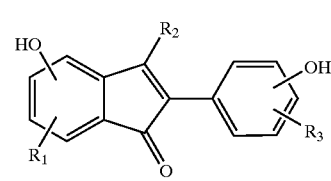

$R^1$, $R^2$, and $R^3$ are as defined in the specification, or a pharmaceutically acceptable salt thereof.

21 Claims, No Drawings

SUBSTITUTED INDENONES AS ESTROGENIC AGENTS

This application claims priority from provisional application Ser. No. 60/341,188, filed Dec. 13, 2001, the entire disclosure of which is hereby incorporated by reference.

BACKGROUND OF THE INVENTION

This invention relates to substituted indenones, which are useful as estrogenic agents.

The pleiotropic effects of estrogens in mammalian tissues have been well documented, and it is now appreciated that estrogens affect many organ systems [Mendelsohn and Karas, New England Journal of Medicine 340: 1801–1811 (1999), Epperson, et al., Psychosomatic Medicine 61: 676–697 (1999), Crandall, Journal of Womens Health & Gender Based Medicine 8: 1155–1166 (1999), Monk and Brodaty, Dementia & Geriatric Cognitive Disorders 11: 1–10 (2000), Hurn and Macrae, Journal of Cerebral Blood Flow & Metabolism 20: 631–652 (2000), Calvin, Maturitas 34: 195–210 (2000), Finking, et al., Zeitschrift fur Kardiologie 89: 442–453 (2000), Brincat, Maturitas 35: 107–117 (2000), Al-Azzawi, Postgraduate Medical Journal 77: 292–304 (2001)]. Estrogens can exert effects on tissues in several ways, and the most well characterized mechanism of action is their interaction with estrogen receptors leading to alterations in gene transcription. Estrogen receptors are ligand-activated transcription factors and belong to the nuclear hormone receptor superfamily. Other members of this family include the progesterone, androgen, glucocorticoid and mineralocorticoid receptors. Upon binding ligand, these receptors dimerize and can activate gene transcription either by directly binding to specific sequences on DNA (known as response elements) or by interacting with other transcription factors (such as AP1), which in turn bind directly to specific DNA sequences [Moggs and Orphamides, EMBO Reports 2: 775–781 (2001), Hall, et al., Journal of Biological Chemistry 276: 36869–36872 (2001), McDonnell, Principles Of Molecular Regulation. p351–361 (2000)]. A class of "coregulatory" proteins can also interact with the ligand-bound receptor and further modulate its transcriptional activity [McKenna, et al., Endocrine Reviews 20: 321–344 (1999)]. It has also been shown that estrogen receptors can suppress NFκB-mediated transcription in both a ligand-dependent and independent manner [Quaedackers, et al., Endocrinology 142: 1156–1166 (2001), Bhat, et al., Journal of Steroid Biochemistry & Molecular Biology 67: 233–240 (1998), Peizer, et al., Biochemical & Biophysical Research Communications 286: 1153–7 (2001)].

Estrogen receptors can also be activated by phosphorylation. This phosphorylation is mediated by growth factors such as EGF and causes changes in gene transcription in the absence of ligand [Moggs and Orphamides, EMBO Reports 2: 775–781 (2001), Hall, et al., Journal of Biological Chemistry 276: 36869–36872 (2001)].

A less well-characterized means by which estrogens can affect cells is through a so-called membrane receptor. The existence of such a receptor is controversial, but it has been well documented that estrogens can elicit very rapid non-genomic responses from cells. The molecular entity responsible for transducing these effects has not been definitively isolated, but there is evidence to suggest it is at least related to the nuclear forms of the estrogen receptors [Levin, Journal of Applied Physiology 91: 1860–1867 (2001), Levin, Trends in Endocrinology & Metabolism 10: 374–377 (1999)].

Two estrogen receptors have been discovered to date. The first estrogen receptor was cloned about 15 years ago and is now referred to as ERα [Green, et al., Nature 320: 134–9 (1986)]. The second form of the estrogen receptor was found comparatively recently and is called ERβ [Kuiper, et al., Proceedings of the National Academy of Sciences of the United States of America 93: 5925–5930 (1996)]. Early work on ERβ focused on defining its affinity for a variety of ligands and indeed, some differences with ERα were seen. The tissue distribution of ERβ has been well mapped in the rodent and it is not coincident with ERα. Tissues such as the mouse and rat uterus express predominantly ERα, whereas the mouse and rat lung express predominantly ERβ [Couse, et al., Endocrinology 138: 4613–4621 (1997), Kuiper, et al., Endocrinology 138: 863–870 (1997)]. Even within the same organ, the distribution of ERα and ERβ can be compartmentalized. For example, in the mouse ovary, ERβ is highly expressed in the granulosa cells and ERα is restricted to the thecal and stromal cells [Sar and Welsch, Endocrinology 140: 963–971 (1999), Fitzpatrick, et al., Endocrinology 140: 2581–2591 (1999)]. However, there are examples where the receptors are coexpressed and there is evidence from in vitro studies that ERα and ERβ can form heterodimers [Cowley, et al., Journal of Biological Chemistry 272: 19858–19862 (1997)].

A large number of compounds have been described that either mimic or block the activity of 17β-estradiol. Compounds having roughly the same biological effects as 17β-estradiol, the most potent endogenous estrogen, are referred to as "estrogen receptor agonists". Those which, when given in combination with 17β-estradiol, block its effects are called "estrogen receptor antagonists". In reality there is a continuum between estrogen receptor agonist and estrogen receptor antagonist activity and indeed some compounds behave as estrogen receptor agonists in some tissues and estrogen receptor antagonists in others. These compounds with mixed activity are called selective estrogen receptor modulators (SERMS) and are therapeutically useful agents (e.g. EVISTA) [McDonnell, Journal of the Society for Gynecologic Investigation 7: S10–S15 (2000), Goldstein, et al., Human Reproduction Update 6: 212–224 (2000)]. The precise reason why the same compound can have cell-specific effects has not been elucidated, but the differences in receptor conformation and/or in the milieu of coregulatory proteins have been suggested.

It has been known for some time that estrogen receptors adopt different conformations when binding ligands. However, the consequence and subtlety of these changes has been only recently revealed. The three dimensional structures of ERα and ERβ have been solved by co-crystallization with various ligands and clearly show the repositioning of helix 12 in the presence of an estrogen receptor antagonist which sterically hinders the protein sequences required for receptor-coregulatory protein interaction [Pike, et al., Embo 18: 4608–4618 (1999), Shiau, et al., Cell 95: 927–937 (1998)]. In addition, the technique of phage display has been used to identify peptides that interact with estrogen receptors in the presence of different ligands [Paige, et al., Proceedings of the National Academy of Sciences of the United States of America 96: 3999–4004 (1999)]. For example, a peptide was identified that distinguished between ERα bound to the full estrogen receptor agonists 17β-estradiol and diethylstilbesterol. A different peptide was shown to distinguish between clomiphene bound to ERα and ERβ. These data indicate that each ligand potentially places the receptor in a unique and unpredictable conformation that is likely to have distinct biological activities.

As mentioned above, estrogens affect a panoply of biological processes. In addition, where gender differences have been described (e.g. disease frequencies, responses to challenge, etc), it is possible that the explanation involves the difference in estrogen levels between males and females.

DESCRIPTION OF THE INVENTION

This invention provides estrogenic compound of formula I having the structure,

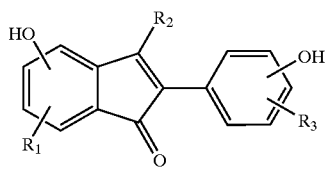

I wherein, $R_1$ is hydrogen, hydroxyl, halogen, trifluroalkyl of 1–6 carbon atoms, alkyl of 1–6 carbon atoms, cycloalkyl of 3–8 carbon atoms, alkenyl of 2–7 carbon atoms, alkoxy of 1–6 carbon atoms, trifluoroalkoxy of 1–6 carbon atoms, thioalkyl of 1–6 carbon atoms, sulfoxoalkyl of 1–6 carbon atoms, sulfonoalkyl of 1–6 carbon atoms, —CN, —NO$_2$, —CHFCN, —CF$_2$CN, aryl of 6–10 carbon atoms, —NR$_4$R$_5$, —NCOR$_4$, —SR$_4$, —SOR$_4$, —SO$_2$R$_4$, or a 5 or 6-membered heterocyclic ring having 1 to 4 heteroatoms selected from O, N or S; wherein the alkyl or alkenyl moieties are optionally substituted with hydroxyl, —CN, halogen, trifluoalkyl of 1–6 carbon atoms, trifluoroalkoxy of 1–6 carbon atoms, —COR$_4$, —CO$_2$R$_4$, —CONR$_4$R$_5$, or NR$_4$R$_5$;

$R_2$ is hydrogen, hydroxyl, alkyl of 1–6 carbon atoms, halogen, phenyl substituted with $R_1$, alkylthio of 1–6 carbon atoms, thioalkyl of 1–6 carbon atoms, amino, aminoalkyl of 1–6 carbon atoms, alkylamino of 1–6 carbon atoms, alkoxy of 1–6 carbon atoms, or alkenyl of 2–7 carbon atoms;

$R_3$ is hydrogen, halogen, hydroxyl, alkyl of 1–6 carbon atoms, alkoxy of 1–6 carbon atoms, trifluoroalkyl of 1–6 carbon atoms, or trifluoroalkoxy of 1–6 carbon atoms;

$R_4$ and $R_5$ are each, independently, hydrogen, alkyl of 1–6 carbon atoms, or aryl of 6–10 carbon atoms;

or a pharmaceutically acceptable salt thereof.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable aids when a compound of this invention contains a basic moiety. Salts may also be formed from organic and inorganic bases, such as alkali metal salts (for example, sodium, lithium, or potassium) alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group, when a compound of this invention contains an acidic moiety.

The terms alkyl, alkenyl, and alkynyl include both branched and straight chain moieties. Examples include methyl, ethyl, propyl, butyl, isopropyl, sec-butyl, tert-butyl, vinyl, allyl, acetylene, 1-methyl vinyl, and the like. When alkyl or alkenyl moieties are substituted, they may typically be mono-, di-, tri- or persubstituted. Examples for a halogen substituent include 1-bromo vinyl, 1-fluoro vinyl, 1,2-difluoro vinyl, 2,2-difluorovinyl, 1,2,2-trifluorovinyl, 1,2-dibromo ethane, 1,2 difluoro ethane, 1-fluoro-2-bromo ethane, $CF_2CF_3$, $CF_2CF_2CF_3$, and the like. The term halogen includes bromine, chlorine, fluorine, and iodine.

The term aryl means phenyl, 1-naphthyl, or 2-naphthyl. Aryl groups may be mono-, di-, or tri-substituted with substituents such as alkyl of 1–6 carbon atoms, alkenyl of 2–7 carbon atoms, halogen, hydroxyl, alkoxy of 1–6 carbon atoms, —CN, —NO$_2$, amino, alkylamino of 1–6 carbon atoms, dialkylamino of 1–6 carbon atoms per alkyl group, thio, alkylthio of 1–6 carbon atoms, alkylsulfinyl of 1–6 carbon atoms, alkylsulfonyl of 1–6 carbon atoms, alkoxycarbonyl of 2–7 carbon atoms, alkylcarbonyl of 2–7 carbon atoms, or benzoyl.

The term alkylthio means —S-alkyl, and the term thioalkyl means -alkyl-SH. Similarly, the term alkylamino means —NH-alkyl, and the term aminoalkyl means -alkyl-NH$_2$. The term trifluoralkyl means -alkyl-CF$_3$.

When $R_2$ is hydroxyl, the resulting compound can exist in the keto and/or enol tautomeric forms; this invention covers both tautomeric forms of such compound.

Preferred 5–6 membered heterocyclic rings include furan, thiophene, pyrrole, isopyrrole, pyrazole, imidazole, triazole, dithiole, oxathiole, isoxazole, oxazole, thiazole, isothiazolem oxadiazole, furazan, oxatriazole, dioxazole, oxathiazole, tetrazole, pyran, pyridine, pyridazine, pyrimidine, pyrazine, triazine, oxazine, oxathiazine, or oxadiazine. It is more preferred that the heterocyclic ring is furan, thiophene, and thiazole.

As used in accordance with this invention, the term "providing," with respect to providing a compound or substance covered by this invention, means either directly administering such a compound or substance, or administering a prodrug, derivative, or analog which will form the effective amount of the compound or substance within the body.

Of the compounds of this invention, it is preferred that $R_3$ is hydrogen; it is more preferred that $R_3$ is hydrogen and $R_1$ is hydrogen, hydroxyl, or alkoxy of 1–6 carbon atoms; and it is most preferred that $R_3$ is hydrogen and $R_1$ is hydrogen, hydroxyl, or alkoxy of 1–6 carbon atoms, and $R_2$ is alkyl of 1–6 carbon atoms, hydroxyl, halogen, alkylamino of 1–6 carbon atoms, alkylthio of 1–6 carbon atoms, or aryl of 6–10 carbon atoms. It is further preferred that the hydroxyl group on the non-indenone ring is para to the attachment of the phenyl ring to the indenone ring system.

The reagents used in the preparation of the compounds of this invention can be either commercially obtained or can be prepared by standard procedures described in the literature.

The compounds of the present invention can be prepared according to the following synthetic Schemes (I–III)

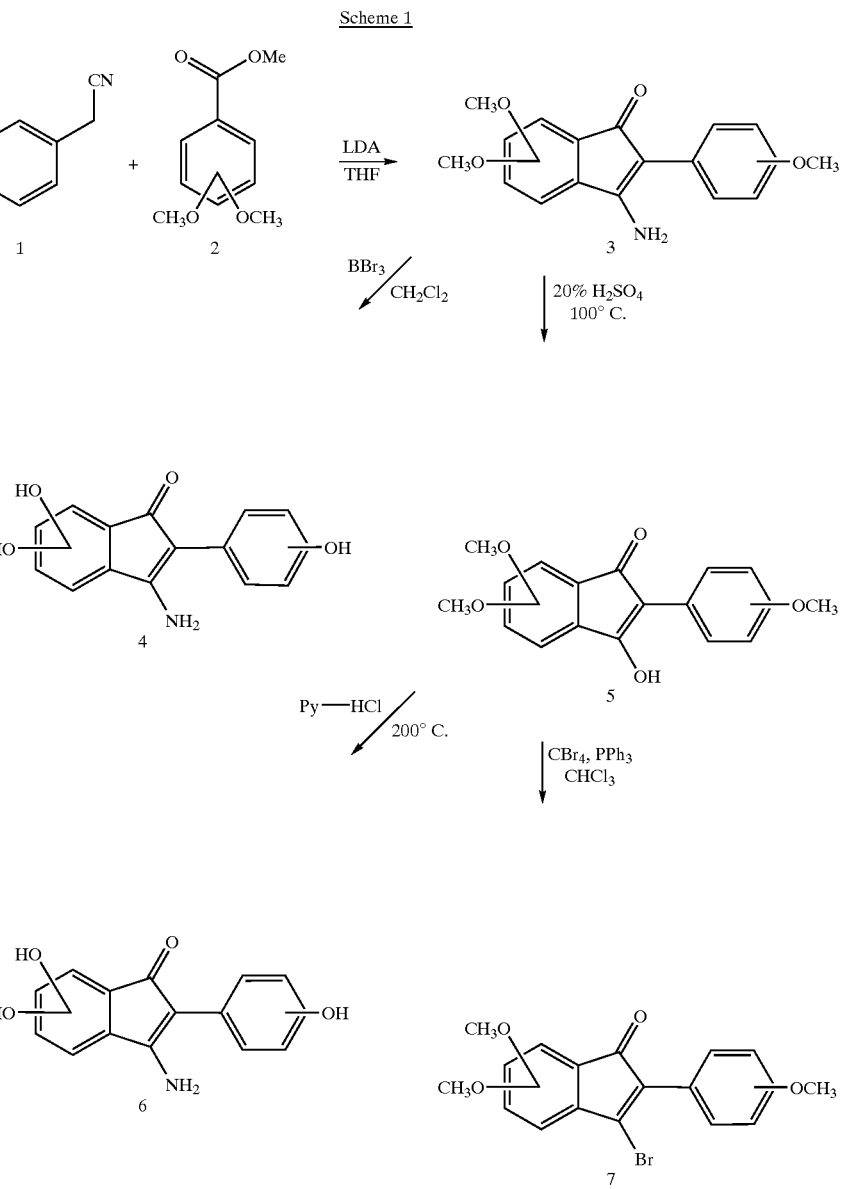

Scheme 1

In Scheme I, commercially available methoxy phenylacetonitrile 1 were treated with commercially available benzoates 2 in the presence of excess LDA to produce indenones 3. Indenones 3 were deprotected with boron tribromide to give the phenolic indenones 4 or converted to the indan-1,3 diones 5 under acid hydrolysis employing 20% sulfuric acid. The dione 5 were converted to the phenolic indandiones 6 upon treatment with pyridine hydrochloride at 200° C. Conversion of the indandiones 5 to the 3-bromoindenone 7 was afforded with carbontetrabromide and triphenyl phosphine.

Scheme II

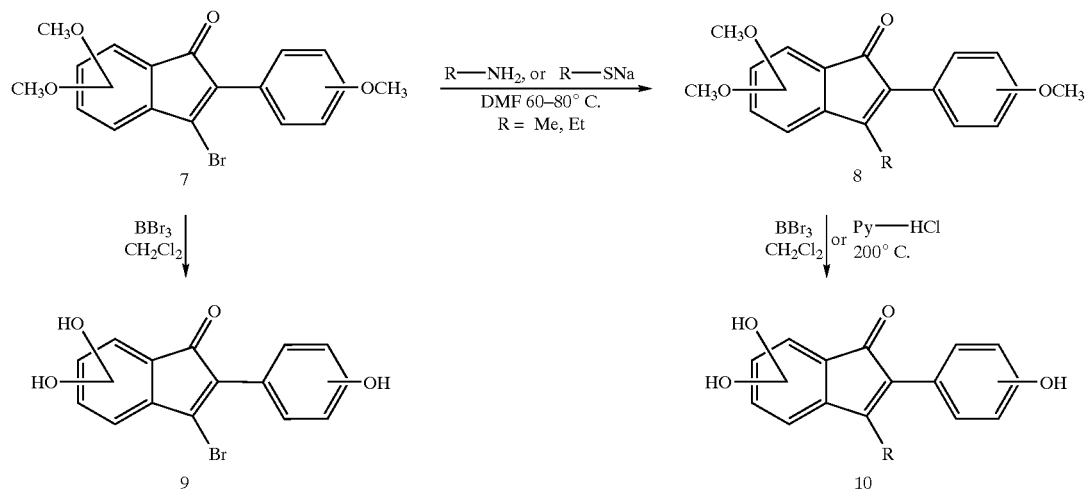

In Scheme II, the 3-bromo-indenone 7 was deprotected or subjected to nucleophilic dislpacement with ether substituted amines or the sodium salts of alkyl thiols to give the substituted indenones 8. Deprotection with either pyridine hydrochloride or boron tribromide gave the final phenolic indenones 9 and 10.

Scheme III

In Scheme III, dione 5 was converted to the 3-substituted indenones 11 upon treatment with sodium hexamethyldisilazane followed by an alkyl grignard or alkyl lithium reagent. Demethylation of 11 with pyridine hydrochloride produced the phenolic indenone 12.

Standard pharmacological test procedures are readily available to determine the activity profile of a given test compound. The following briefly summarizes several representative test procedures and may include data for representative compounds of the invention. All assays, except the radioligand binding assay, can be used to detect estrogen receptor agonist or antagonist activity of compounds. In general, estrogen receptor agonist activity is measured by comparing the activity of the compound to a reference estrogen (e.g. 17β-estradiol, 17α-ethinyl,17β-estradiol, estrone, diethylstilbesterol etc). Estrogen receptor antagonist activity is generally measured by co-treating the test compound with the reference estrogen and comparing the result to that obtained with the reference estrogen alone. Standard pharmacological test procedures for SERMs are also provided in U.S. Pat. Nos. 4,418,068 and 5,998,402 which are hereby incorporated by reference.

Evaluation of Binding Affinities to ERα and ERβ

Representative examples of the invention were evaluated for their ability to compete with 17β-estradiol for both ERα and ERβ in a conventional radioligand binding assay. This test procedure provides the methodology for one to determine the relative binding affinities for the ERα or ERβ receptors. The procedure used is briefly described below.

Preparation of receptor extracts for characterization of binding selectivity. The ligand binding domains, conveniently defined here as all sequence downstream of the DNA binding domain, were obtained by PCR using full length cDNA as templates and primers that contained appropriate restriction sites for subcloning while maintaining the appropriate reading frame for expression. These templates contained amino acids $M_{250}$–$V_{595}$ of human ERα [Green, et al., Nature 320: 134–9 (1986)] and $M_{214}$–$Q_{530}$ of human ERβ [Ogawa, et al., Biochemical & Biophysical Research Communications 243: 122–6 (1998)]. Human ERβ was cloned into pET15b (Novagen, Madison Wis.) as a Nco1-BamH1 fragment bearing a C-terminal Flag tag. Human ERα was cloned as for human ERβ except that an N-terminal His tag was added. The sequences of all constructs used were verified by complete sequencing of both strands.

BL21(DE3) cells were used to express the human proteins. Typically a 10 mL overnight culture was used to inoculate a 1 L culture of LB medium containing 100 μg/mL of ampicillin. After incubation overnight at 37° C., IPTG was added to a final concentration of 1 mM and incubation proceeded at 25° C. for 2 hours. Cells were harvested by centrifugation (1500×g), and the pellets washed with and resuspended in 100 mL of 50 mM Tris-Cl (pH 7.4), 150 mM NaCl. Cells were lysed by passing twice through a French press at 12000 psi. The lysate was clarified by centrifugation at 12,000×g for 30 minutes at 4° C. and stored at −70° C.

Evaluation of extracts for specific [$^3$H]-estradiol binding. Dulbecco's phosphate buffered saline (Gibco, 1×final concentration) supplemented with 1 mM EDTA was used as the assay buffer. To optimize the amount of receptor to use in the assay, [$^3$H]-17β-estradiol (New England Nuclear; final concentration=2 nM)±0.6 μM diethlystilbestrol and 100 μL of various dilutions of the E. coli lysate were added to each well of a high binding masked microtiter plate (EG&G Wallac). The final assay volume was 120 μL and the concentration of DMSO was ≦1%. After incubation at room temperature for 5–18 hours, unbound material was aspirated and the plate washed three times with approximately 300 μL of assay buffer. After washing, 135 μL of scintillation cocktail (Optiphase Supermix, EG&G Wallac) was added to the wells, and the plate was sealed and agitated for at least 5 minutes to mix scintillant with residual wash buffer. Bound radioactivity was evaluated by liquid scintillation counting (EG&G Wallac Microbeta Plus).

After determining the dilution of each receptor preparation that provided maximum specific binding, the assay was further optimized by estimating the $IC_{50}$ of unlabelled 17β-estradiol using various dilutions of the receptor preparation. A final working dilution for each receptor preparation was chosen for which the $IC_{50}$ of unlabelled 17β-estradiol was 2–4 nM.

Ligand binding competition test procedure. Test compounds were initially solubilized in DMSO and the final concentration of DMSO in the binding assay was <1%. Eight dilutions of each test compound were used as an unlabelled competitor for [$^3$H]-17β-estradiol. Typically, a set of compound dilutions would be tested simultaneously on human ERα and ERβ. The results were plotted as measured DPM vs. concentration of test compound. For dose-response curve fitting, a four parameter logistic model on the transformed, weighted data was fit and the $IC_{50}$ was defined as the concentration of compound decreasing maximum [$^3$H]-estradiol binding by 50%.

Binding affinities for ERα and ERβ (as measured by $IC_{50}$) for representative examples of the invention are shown in Table (1).

TABLE 1

Estrogen receptor binding affinities of compounds of the invention

| Example | ER-β $IC_{50}$ (μM) | ER-α $IC_{50}$ (μM) |
|---|---|---|
| 1 | 1.15 | >5.0 |
| 2 | 2.63 | >5.0 |
| 3 | 0.02 | 0.290 |
| 4 | 0.002 | 0.005 |
| 5 | 2.70 | >5.0 |
| 6 | 0.008 | 0.01 |
| 7 | 0.150 | 0.40 |
| 8 | 0.003 | 0.012 |
| 9 | 0.001 | 0.003 |
| 10 | 0.008 | 0.01 |
| 11 | 0.005 | 0.015 |
| 12 | 0.011 | 0.055 |
| 13 | 0.002 | 0.006 |
| 14 | 1.38 | >5.0 |
| 15 | 0.267 | 0.714 |
| 16 | 0.150 | 0.200 |
| 17 | 0.002 | 0.031 |
| 18 | 0.150 | 0.500 |
| 19 | 0.002 | 0.003 |
| 20 | 0.044 | 0.047 |
| 21 | 0.003 | 0.003 |
| 22 | 0.131 | 0.076 |

The results obtained in the standard pharmacologic test procedure described above demonstrate that the compounds of this invention bind both subtypes of the estrogen receptor. The $IC_{50}$s are generally lower for ERβ, indicating these compounds are preferentially ERβ selective ligands, but are still considered active at ERα. Compounds of this invention will exhibit a range of activity based, at least partially, on their receptor affinity selectivity profiles. Since the compounds of the invention bind ER-β with higher affinity than ER-α, they will be useful in treating or inhibiting diseases that can be modulated via ER-β. Additionally, since each receptor ligand complex is unique and thus its interaction with various coregulatory proteins is unique, compounds of this invention will display different and unpredictable activities depending on cellular context. For example, in some cell-types, it is possible for a compound to behave as an estrogen receptor agonist while in other tissues, an estrogen receptor antagonist. Compounds with such activity have sometimes been referred to as SERMs (Selective Estrogen Receptor Modulators). Unlike many estrogens, however, many of the SERMs do not cause increases in uterine wet weight. These compounds are antiestrogenic in the uterus and can completely antagonize the trophic effects of estrogen receptor agonists in uterine tissue. These compounds, however, act as estrogen receptor agonists in the bone, cardiovascular, and central nervous systems. Due to this tissue selective nature of these compounds, they are useful in treating or inhibiting in a mammal disease states or syndromes which are caused or associated with an estrogen deficiency (in certain tissues such as bone or cardiovascular) or an excess of estrogen (in the uterus or mammary glands). In addition, compounds of this invention also have the potential to behave as estrogen receptor agonists on one receptor type while behaving as estrogen receptor antagonists on the other. For example, it has been demonstrated that compounds can be antagonize the action of 17β-estradiol via ERβ while exhibiting estrogen receptor agonist activity with ERα [Sun, et al., Endocrinology 140: 800–804 (1999)]. Such ERSAA (Estrogen Receptor Selective Agonist Antagonist) activity provides for pharmacologically distinct estrogenic activity within this series of compounds Regulation of Metallothionein II mRNA Estrogens acting through ERβ, but not ERα can upregulate metallothionein II mRNA levels in Saos-2 cells as described by Harris [Endocrinology 142: 645–652 (2001)]. Results from this test procedure can be combined with results from the test procedure described below (ERE reporter test procedure) to generate a selectivity profile for compounds of this invention (see also WO 00/37681). Data for representative compounds of the invention are shown in Table (2).

TABLE 2

Upregulation of metallothionein-II mRNA in Saos-2 cells by selected compounds of the invention

| Example | Fold upregulation |
| --- | --- |
| 3 | 10.8 |
| 4 | 10.4 |
| 15 | 5.6 |

Evaluation of Test Compound Using an ERE-reporter Test Procedure in MCF-7 Breast Cancer Cells Stock solutions of test compounds (usually 0.1 M) are prepared in DMSO and then diluted 10 to 100-fold with DMSO to make working solutions of 1 or 10 mM. The DMSO stocks are stored at either 4° C. (0.1 M) or −20° C. (<0.1M). MCF-7 cells are passaged twice a week with growth medium [D-MEM/F-12 medium containing 10% (v/v) heat-inactivated fetal bovine serum, 1% (v/v) Penicillin-Streptomycin, and 2 mM glutaMax-1]. The cells are maintained in vented flasks at 37° C. inside a 5% $CO_2$/95% humidified air incubator. One day prior to treatment, the cells are plated with growth medium at 25,000 cells/well into 96 well plates and incubated at 37° C. overnight.

The cells are infected for 2 hr at 37° C. with 50 μl/well of a 1:10 dilution of adenovirus 5-ERE-tk-luciferase in experimental medium [phenol red-free D-MEM/F-12 medium containing 10% (v/v) heat-inactived charcoal-stripped fetal bovine serum, 1% (v/v) Penicillin-Streptomycin, 2 mM glutaMax-1, 1 mM sodium pyruvate]. The wells are then washed once with 150 μl of experimental medium. Finally, the cells are treated for 24 hr at 37° C. in replicates of 8 wells/treatment with 150 μl/well of vehicle (≦0.1% v/v DMSO) or compound that is diluted ≧1000-fold into experimental medium.

Initial screening of test compounds is done at a single dose of 1 μM that is tested alone (estrogen receptor agonist mode) or in combination with 0.1 nM 17β-estradiol ($EC_{80}$; estrogen receptor antagonist mode). Each 96 well plate also includes a vehicle control group (0.1% v/v DMSO) and an estrogen receptor agonist control group (either 0.1 or 1 nM 17β-estradiol). Dose-response experiments are performed in either the estrogen receptor agonist and/or estrogen receptor antagonist modes on active compounds in log increases from $10^{-14}$ to $10^{-5}$ M. From these dose-response curves, $EC_{50}$ and $IC_{50}$ values, respectively, are generated. The final well in each treatment group contains 5 μl of $3 \times 10^{-5}$ M ICI-182,780 ($10^{-6}$ M final concentration) as an estrogen receptor antagonist control.

After treatment, the cells are lysed on a shaker for 15 min with 25 μl/well of 1×cell culture lysis reagent (Promega Corporation). The cell lysates (20 μl) are transferred to a 96 well luminometer plate, and luciferase activity is measured in a MicroLumat LB 96 P luminometer (EG & G Berthold) using 100 μl/well of luciferase substrate (Promega Corporation). Prior to the injection of substrate, a 1 second background measurement is made for each well. Following the injection of substrate, luciferase activity is measured for 10 seconds after a 1 second delay. The data are transferred from the luminometer to a Macintosh personal computer and analyzed using the JMP software (SAS Institute); this program subtracts the background reading from the luciferase measurement for each well and then determines the mean and standard deviation of each treatment.

The luciferase data are transformed by logarithms, and the Huber M-estimator is used to down-weight the outlying transformed observations. The JMP software is used to analyze the transformed and weighted data for one-way ANOVA (Dunnett's test). The compound treatments are compared to the vehicle control results in the estrogen receptor agonist mode, or the positive estrogen receptor agonist control results (0.1 nM 17β-estradiol) in the estrogen receptor antagonist mode. For the initial single dose experiment, if the compound treatment results are significantly different from the appropriate control (p<0.05), then the results are reported as the percent relative to the 17β-estradiol control [i.e., ((compound−vehicle control)/(17β-estradiol control−vehicle control))×100]. The JMP software is also used to determine the $EC_{50}$ and/or $IC_{50}$ values from the non-linear dose-response curves.

Evaluation of Uterotrophic Activity

Uterotrophic activity of a test compound can be measured according to the following standard pharmacological test procedures.

Procedure 1: Sexually immature (18 days of age) Sprague-Dawley rats are obtained from Taconic and provided unrestricted access to a casein-based diet (Purina Mills 5K96C) and water. On day 19, 20 and 21 the rats are dosed subcutaneously with 17α-ethinyl-17β-estradiol (0.06 μg/rat/day), test compound or vehicle (50% DMSO/50% Dulbecco's PBS). To assess estrogen receptor antagonist, compounds are coadministered with 17α-ethinyl-17β-estradiol (0.06 μg/rat/day). There are six rats/group and they are euthanized approximately 24 hours after the last injection by $CO_2$ asphyxiation and pneumothorax. Uteri are removed and weighed after trimming associated fat and expressing any internal fluid. A tissue sample can also be snap frozen for analysis of gene expression (e.g. complement factor 3 mRNA).

Procedure 2: Sexually immature (18 days of age) 129 SvE mice are obtained from Taconic and provided unrestricted access to a casein-based diet (Purina Mills 5K96C) and water. On day 22, 23, 24 and 25 the mice are dosed subcutaneously with compound or vehicle (corn oil). There are six mice/group and they are euthanized approximately 6 hours after the last injection by $CO_2$ asphyxiation and pneumothorax. Uteri are removed and weighed after trimming associated fat and expressing any internal fluid.

Evaluation of Osteoporosis and Lipid Modulation (Cardioprotection)

Female Sprague-Dawley rats, ovariectomized or sham operated, are obtained 1 day after surgery from Taconic Farms (weight range 240–275 g). They are housed 3 or 4 rats/cage in a room on a 12/12 (light/dark) schedule and provided with food (Purina 5K96C rat chow) and water ad libitum. Treatment for all studies begin 1 day after arrival and rats are dosed 7 days per week as indicated for 6 weeks. A group of age matched sham operated rats not receiving any treatment serve as an intact, estrogen replete control group for each study.

All test compounds are prepared in a vehicle of 50% DMSO (J T Baker, Phillipsburg, N.J.)/1×Dulbecco's phosphate saline (GibcoBRL, Grand Island, N.Y.) at defined concentrations so that the treatment volume is 0.1 mL/100 g body weight. 17β-estradiol is dissolved in corn oil (20 μg/mL) and delivered subcutaneously, 0.1 mL/rat. All dosages are adjusted at three week intervals according to group mean body weight measurements, and given subcutaneously.

Five weeks after the initiation of treatment and one week prior to the termination of the study, each rat is evaluated for bone mineral density (BMD). The total and trabecular density of the proximal tibia are evaluated in anesthetized rats using an XCT-960M (pQCT; Stratec Medizintechnik, Pforzheim, Germany). The measurements are performed as follows: Fifteen minutes prior to scanning, each rat is anesthetized with an intraperitoneal injection of 45 mg/kg ketamine, 8.5 mg/kg xylazine, and 1.5 mg/kg acepromazine.

The right hind limb is passed through a polycarbonate tube with a diameter of 25 mm and taped to an acrylic frame with the ankle joint at a 900 angle and the knee joint at 180°. The polycarbonate tube is affixed to a sliding platform that maintains it perpendicular to the aperture of the pQCT. The platform is adjusted so that the distal end of the femur and the proximal end of the tibia is in the scanning field. A two dimensional scout view is run for a length of 10 mm and a line resolution of 0.2 mm. After the scout view is displayed on the monitor, the proximal end of the tibia is located. The pQCT scan is initiated 3.4 mm distal from this point. The pQCT scan is 1 mm thick, has a voxel (three dimensional pixel) size of 0.140 mm, and consists of 145 projections through the slice.

After the pQCT scan is completed, the image is displayed on the monitor. A region of interest including the tibia but excluding the fibula is outlined. The soft tissue is mathematically removed using an iterative algorithm. The density of the remaining bone (total density) is reported in mg/cm$^3$. The outer 55% of the bone is mathematically peeled away in a concentric spiral. The density of the remaining bone (Trabecular density) is reported in mg/cm$^3$.

One week after BMD evaluation the rats are euthanized by $CO_2$ asphyxiation and pneumothorax, and blood is collected for cholesterol determination. The uteri are also removed and the weighed after trimming associated fat and expressing any luminal fluid. Total cholesterol is determined using a Boehringer-Mannheim Hitachi 911 clinical analyzer using the Cholesterol/HP kit. Statistics were compared using one-way analysis of variance with Dunnet's test.

Evaluation of Antioxidant Activity

Porcine aortas are obtained from an abattoir, washed, transported in chilled PBS, and aortic endothelial cells are harvested. To harvest the cells, the intercostal vessels of the aorta are tied off and one end of the aorta clamped. Fresh, sterile filtered, 0.2% collagenase (Sigma Type I) is placed in the vessel and the other end of the vessel then clamped to form a closed system. The aorta is incubated at 37° C. for 15–20 minutes, after which the collagenase solution is collected and centrifuged for 5 minutes at 2000×g. Each pellet is suspended in 7 mL of endothelial cell culture medium consisting of phenol red free DMEM/Ham's F12 media supplemented with charcoal stripped FBS (5%), NuSerum (5%), L-glutamine (4 mM), penicillin-streptomycin (1000 U/ml, 100 µg/ml) and gentamycin (75 µg/ml), seeded in 100 mm petri dish and incubated at 37° C. in 5% $CO_2$. After 20 minutes, the cells are rinsed with PBS and fresh medium added, this was repeated again at 24 hours. The cells are confluent after approximately 1 week. The endothelial cells are routinely fed twice a week and, when confluent, trypsinized and seeded at a 1:7 ratio. Cell mediated oxidation of 12.5 µg/mL LDL is allowed to proceed in the presence of the compound to be evaluated (5 µM) for 4 hours at 37° C. Results are expressed as the percent inhibition of the oxidative process as measured by the TBARS (thiobarbituric acid reactive substances) method for analysis of free aldehydes [Yagi, Biochemical Medicine 15: 212–6 (1976)].

Progesterone Receptor mRNA Regulation Standard Pharmacological Test Procedure

This test procedure can be used to evaluate the estrogenic or antiestrogenic activity of compounds from this invention [Shughrue, et al., Endocrinology 138: 5476–5484 (1997)].

Rat Hot Flush Test Procedure

The effect of test compounds on hot flushes can be evaluated in a standard pharmacological test procedure which measures the ability of a test compound to blunt the increase in tail skin temperature which occurs as morphine-addicted rats are acutely withdrawn from the drug using naloxone [Merchenthaler, et al., Maturitas 30: 307–16 (1998)]. It can also be used to detect estrogen receptor antagonist activity by co-dosing test compound with the reference estrogen.

Evaluation of Vasomotor Function in Isolated Rat Aortic Rings

Sprague-Dawley rats (240–260 grams) are divided into 4 groups:
1. Normal non-ovariectomized (intact)
2. Ovariectomized (ovex) vehicle treated
3. Ovariectomized 17β-estradiol treated (1 mg/kg/day)
4. Ovariectomized animals treated with test compound (various doses)

Animals are ovariectomized approximately 3 weeks prior to treatment. Each animal receives either 17-β estradiol sulfate (1 mg/kg/day) or test compound suspended in distilled, deionized water with 1% tween-80 by gastric gavage. Vehicle treated animals received an appropriate volume of the vehicle used in the drug treated groups.

Animals are euthanized by $CO_2$ inhalation and exsanguination. Thoracic aortae are rapidly removed and placed in 37° C. physiological solution with the following composition (mM): NaCl (54.7), KCl (5.0), $NaHCO_3$ (25.0), $MgCl_2$ $2H_2O$ (2.5), D-glucose (11.8) and $CaCl_2$ (0.2) gassed with $CO_2$—$O_2$, 95%/5% for a final pH of 7.4. The advantitia is removed from the outer surface and the vessel is cut into 2–3 mm wide rings. Rings are suspended in a 10 mL tissue bath with one end attached to the bottom of the bath and the other to a force transducer. A resting tension of 1 gram is placed on the rings. Rings are equilibrated for 1 hour, signals are acquired and analyzed.

After equilibration, the rings are exposed to increasing concentrations of phenylephrine ($10^{-8}$ to $10^{-4}$ M) and the tension recorded. Baths are then rinsed 3 times with fresh buffer. After washout, 200 mM L-NAME is added to the tissue bath and equilibrated for 30 minutes. The phenylephrine concentration response curve is then repeated.

Evaluation of Cardioprotective Activity

Apolipoprotein E-deficient C57/B1J (apo E KO) mice are obtained from Taconic Farms. All animal procedures are performed under strict compliance to IACUC guidelines. Ovariectomized female apo E KO mice, 4–7 weeks of age, are housed in shoe-box cages and were allowed free access to food and water. The animals are randomized by weight into groups (n=12–15 mice per group). The animals are dosed with test compounds or estrogen (17β-estradiol sulfate at 1 mg/kg/day) in the diet using a Precise-dosing Protocol, where the amount of diet consumed is measured weekly, and the dose adjusted accordingly, based on animal weight. The diet used is a Western-style diet (57U5) that is prepared by Purina and contains 0.50% cholesterol, 20% lard and 25 IU/KG Vitamin E. The animals are dosed/fed using this paradigm for a period of 12 weeks. Control animals are fed the Western-style diet and receive no compound. At the end of the study period, the animals are euthanized and plasma samples obtained. The hearts are perfused in situ, first with saline and then with neutral buffered 10% formalin solution.

For the determination of plasma lipids and lipoproteins, total cholesterol and triglycerides are determined using enzymatic methods with commercially available kits from Boehringer Mannheim and Wako Biochemicals, respectively and analyzed using the Boehringer Mannheim Hitachii 911 Analyzer. Separation and quantification of plasma lipoproteins were performed using FPLC size fractionation. Briefly, 50–100 mL of serum is filtered and injected into Superose 12 and Superose 6 columns connected in series and eluted at a constant flow rate with 1 mM sodium EDTA and 0.15 M NaCl. Areas of each curve representing VLDL, LDL and HDL are integrated using Waters Millennium™ software, and each lipoprotein fraction is quantified by multiplying the Total Cholesterol value by the relative percent area of each respective chromatogram peak.

For the quantification of aortic atherosclerosis, the aortas are carefully isolated and placed in formalin fixative for 48–72 hours before handling. Atherosclerotic lesions are identified using Oil Red O staining. The vessels are briefly destained, and then imaged using a Nikon SMU800 microscope fitted with a Sony 3CCD video camera system in concert with IMAQ Configuration Utility (National Instrument) as the image capturing software. The lesions are quantified en face along the aortic arch using a custom threshold utility software package (Coleman Technologies). Automated lesion assessment is performed on the vessels using the threshold function of the program, specifically on the region contained within the aortic arch from the proximal edge of the brachio-cephalic trunk to the distal edge of the left subclavian artery. Aortic atherosclerosis data are expressed as percent lesion involvement strictly within this defined luminal area.

Evaluation of Cognition Enhancement

Ovariectomized rats (n=50) are habituated to an 8-arm radial arm maze for 10-min periods on each of 5 consecutive days. Animals are water-deprived prior to habituation and testing. A 100 μL aliquot of water placed at the ends of each arm serves as reinforcement. Acquisition of a win-shift task in the radial arm maze is accomplished by allowing the animal to have access to one baited arm. After drinking, the animal exits the arm and re-enters the central compartment, where it now has access to the previously visited arm or to a novel arm. A correct response is recorded when the animal chooses to enter a novel arm. Each animal is given 5 trials per day for 3 days. After the last acquisition trial, the animals are assigned to one of the following 4 groups:

1. Negative controls: injected with 10% DMSO/sesame oil vehicle once daily for 6 days (1 mL/kg, SC)
2. Positive controls: injected with 17β-estradiol benzoate for 2 days and tested 4 days after the second injection (17β-estradiol benzoate at 10 μg/0.1 mL per rat)
3. Estradiol: 17β-estradiol will be injected daily for 6 days (20 μg/kg, SC)
4. Test compound: injected daily for 6 days (doses vary). All injections will begin after testing on the last day of acquisition. The last injection for groups 1, 3, and 4 will take place 2 hours before testing for working memory.

The test for working memory is a delayed non-matching-to-sample task (DNMS) utilizing delays of 15, 30, or 60 seconds. This task is a variation of the acquisition task in which the rat is placed in the central arena and allowed to enter one arm as before. A second arm is opened once the rat traverses halfway down the first arm, and again the rat is required to choose this arm. When it has traveled halfway down this second arm, both doors are closed and the delay is instituted. Once the delay has expired, both of the original two doors, and a third novel door, are opened simultaneously. A correct response is recorded when the animal travels halfway down the third, novel arm. An incorrect response is recorded when the animal travels halfway down either the first or second arms. Each animal will receive 5 trials at each of the three delay intervals for a total of 15 trials per subject.

Evaluation of Effect on Pleurisy

The ability to reduce the symptoms of experimentally-induced pleurisy in rats can be evaluated according to the procedure of Cuzzocrea [Endocrinology 141: 1455–63 (2000)].

Evaluation of Protection Against Glutamate-Induced Cytotoxicity (Neuroprotection)

The neuroprotective activity of compounds of this invention can be evaluated in an in vitro standard pharmacological test procedure using glutamate challenge [Zaulyanov, et al., Cellular & Molecular Neurobiology 19: 705–18 (1999); Prokai, et al., Journal of Medicinal Chemistry 44: 110–4 (2001)].

Evaluation in the Mammary End Bud Test Procedure

Estrogens are required for full ductal elongation and branching of the mammary ducts, and the subsequent development of lobulo-alveolar end buds under the influence of progesterone. In this test procedure, the mammotrophic activity of selected compounds of the invention can be evaluated according to the following standard pharmacological test procedure. Twenty-eight day old Sprague-Dawley rats (Taconic Farms, Germantown, N.Y.) are ovariectomized and rested for nine days. Animals are housed under a 12-hour light/dark cycle, fed a casein-based Purina Laboratory Rodent Diet 5K96 (Purina, Richmond, Ind.) and allowed free access to water. Rats were then dosed subcutaneously for six days with vehicle (50% DMSO (J T Baker, Phillipsburg, N.J.)/50% 1×Dulbecco's Phosphate buffered saline (GibcoBRL, Grand Island, N.Y.), 17β-estradiol (0.1 mg/kg) or test compound (20 mg/kg). For the final three days, rats are also dosed subcutaneously with progesterone (30 mg/kg). On the seventh day, rats are euthanised and a mammary fat pad excised. This fat pad is analyzed for casein kinase II mRNA as a marker of end bud proliferation. Casein kinase II mRNA is anlayzed by real-time RT-PCR. Briefly, RNA is isolated following Trizol (GibcoBRL, Grand Island, N.Y.) according to the manufacture's directions, Samples are treated with DNAse I using DNA-free kit (Ambion), and casein kinase II mRNA levels are measured by real-time RT-PCR using the Taqman Gold procedure (PE Applied Biosystems). A total of 50 ng of RNA is analyzed in triplicate using casein kinase II specific primer pair (5' primer, CACACGGATGGCGCATACT; 3' primer, CTCGGGATGCACCATGAAG) and customized probe (TAMRA-CGGCACTGGTTTCCCTCACATGCT-FAM). Casein kinase II mRNA levels are normalized to 18s ribosomal RNA contained within each sample reaction using primers and probe supplied by PE Applied Biosystems.

Evaluation in the HLA Rat Standard Pharmacological Test Procedure for Inflammatory Bowel Disease Representative compounds can be evaluated in the HLA rat standard pharmacological test procedure which emulates inflammatory bowel disease in humans. The following briefly describes the procedure used and results obtained. Male HLA-B27 rats are obtained from Taconic and provided unrestricted access to food (PMl Lab diet 5001) and water. Stool quality is observed daily and graded according to the following scale: Diarrhea=3; soft stool=2; normal stool=1.

At the end of the study, serum is collected and stored at −70° C. A section of colon is prepared for histological analysis and an additional segment is analyzed for myeloperoxidase activity.

Histological analysis. Colonic tissue is immersed in 10% neutral buffered formalin. Each specimen of colon is separated into four samples for evaluation. The formalin-fixed tissues are processed in a Tissue Tek vacuum infiltration processor (Miles, Inc; West Haven, Conn.) for paraffin embedding. The samples are sectioned at 5 µm and then stained with hematoxylin and eosin (H&E) for blinded histologic evaluations using a scale modified after Boughton-Smith. After the scores are completed the samples are unblinded, and data are tabulated and analyzed by ANOVA linear modeling with multiple mean comparisons. Sections of colonic tissue are evaluated for several disease indicators and given relative scores.

Evaluation in Two Models of Arthritis

Lewis rat assay of adjuvant-induced arthritis. Sixty, female, 12 weeks old, Lewis rats are housed according to standard facility operating procedures. They receive a standard regimen of food and water ad libitum. Each animal is identified by a cage card indicating the project group and animal number. Each rat number is marked by indelible ink marker on the tail. At least 10–21 days before study they are anesthetized and ovariectomized by standard aseptic surgical techniques.

Freund's Adjuvant-Complete (Sigma Immuno Chemicals, St. Louis, Mo.) is used to induce arthritis, each mL containing 1 mg *Mycobacterium tuberculosis* heat killed and dried, 0.85 mL mineral oil and 0.15 mL mannide monooleate Lot No. 084H8800.

The following are examples of two test procedures. Inhibition test procedure: Thirty rats are injected intradermally with 0.1 mL of Freund's Adjuvant-Complete at the base of the tail. The animals are randomized to four groups, each group containing six rats. Each day, the groups receive vehicle (50% DMSO (J T Baker, Phillipsburg, N.J.)/1× Dulbecco's phosphate saline (GibcoBRL, Grand Island, N.Y.)) or test compound (administered subcutaneously). All rats begin treatment on Day 1.

Treatment test procedure: Thirty rats are injected intradermally with 0.1 mL of Freund's Adjuvant-Complete at the base of the tail. The animals are randomized to four groups, each group containing six rats. Each day, the groups receive vehicle (50% DMSO (J T Baker, Phillipsburg, N.J.)/1× Dulbecco's phosphate saline (GibcoBRL, Grand Island, N.Y.)) or test compound (administered subcutaneously). All rats begin treatment on Day 8 after adjuvant injection.

Statistical analysis is performed using Abacus Concepts Super ANOVA. (Abacus Concepts, Inc., Berkeley, Calif.). All of the parameters of interest are subjected to Analysis of Variance with Duncan's new multiple range post hoc testing between groups. Data are expressed throughout as mean±standard deviation (SD), and differences are deemed significant if $p<0.05$.

The degree of arthritis severity is monitored daily in terms of the following disease indices: Hindpaw erythema, hindpaw swelling, tenderness of the joints, and movements and posture. An integer scale of 0 to 3 is used to quantify the level of erythema (0=normal paw, 1=mild erythema, 2=moderate erythema, 3=severe erythema) and swelling (0=normal paw, 1=mild swelling, 2=moderate swelling, 3=severe swelling of the hind paw). The maximal score per day is 12.

At the end of the study the rats are euthanized with $CO_2$, hindlimbs removed at necropsy and fixed in 10% buffered formalin, and the tarsal joints decalcified and embedded in paraffin. Histologic sections are stained with Hematoxylin and Eosin or Saffranin O—Fast Green stain.

Slides are coded so that the examiner is blinded to the treatment groups. Synovial tissue from tarsal joints is evaluated based on synovial hyperplasia, inflammatory cell infiltration, and pannus formation [Poole and Coombs, International Archives of Allergy & Applied Immunology 54: 97–113 (1977)] as outlined below.

| Category | Grade |
| --- | --- |
| 1. Synovial lining cells | |
| a. No change | 0 |
| b. Cells enlarged, slightly thickened | 1 |
| c. Cells enlarged, increase in numbers, moderately thickened. No villus present | 2 |
| d. Cells enlarged, thickened. VillIus present | 3 |
| 2. Fibroplasia | |
| a. No change | |
| b. Fibroplasia present under lining cells | 1 |
| c. Small areas of areolar tissue replaced by fibrous tissue | 2 |
| d. Replacement of areolar tissue by fibrous tissue | 3 |
| 3. Inflammatory cells | |
| a. Occasionally seen, scattered throughout selection | 0 |
| b. Cells present in small numbers in or just under lining cell layer and/or around blood vessels. | 1 |
| c. Small focal collection of cells may be present | 2 |
| d. Large numbers of cells present in capsule and in or under lining cell layers. Large foci often seen. | 3 |
| 4. Pannus | |
| a. Not detectable | 0 |
| b. Detectable | 1 |

In addition, articular cartilage and bone is evaluated using Mankin's histological grading system [Mankin, et al., Journal of Bone & Joint Surgery—American Volume 53: 523–37 (1971)] as shown below.

| Category | Grade |
| --- | --- |
| 1. Structure | |
| a. Normal | 0 |
| b. Surface irregularity | 1 |
| c. Pannus and surface irregularity | 2 |
| d. Clefts to transitional zone | 3 |
| e. Clefts to radial zone | 4 |
| f. Clefts to calcified zone | 5 |
| g. Complete disorganization | 6 |
| 2. Cells | |
| a. Normal | 0 |
| b. Diffuse hypercellularity | 1 |
| c. Cloning | 2 |
| d. Hypocellularity | 3 |
| 3. Safranin-O staining | |
| a. Normal | 0 |
| b. Slight reduction | 1 |
| c. Modest reduction | 2 |
| d. Severe reduction | 3 |
| e. No dye noted | 4 |
| 4. Tidemark integrity | |
| a. Intact | 0 |
| b. Crossed by blood vessels | 1 |

Evaluation in the HLA-B27 Rat model of arthritis. Representative compounds are evaluated in the HLA-B27 rat standard pharmacological test procedure which emulates arthritis in humans. The following briefly describes the procedure used. Male HLA-B27 rats are obtained from Taconic and provided unrestricted access to a food (PMI Lab diet 5001) and water. Joint scores and histology are evaluated as described above for the Lewis rat model of adjuvant-induced arthritis.

Evaluation in in vivo Models of Carcinogeneisis

The ability of compounds of this invention to treat and inhibit various malignancies or hyperprolific disorders can be evaluated in standard pharmacological test procedures that are readily available in the literature, and include the following two procedures.

Breast cancer. Athymic nu/nu (nude) mice are obtained ovariectomized from Charles River Laboratories (Wilmington, Mass.). One day prior to tumor cell injection, animals are implanted with time-release pellets containing 0.36–1.7 mg 17β-estradiol (60 or 90 day release, Innovative Research of America, Sarasota, Fla.) or a placebo. The pellet is introduced subcutaneously into the intrascapular region using a 10-gauge precision trochar. Subsequently, mice are injected subcutaneously into the breast tissue with either $1 \times 10^7$ MCF-7 cells or $1 \times 10^7$ BG-1 cells. The cells are mixed with an equal volume of matrigel, a basement membrane matrix preparation to enhance tumor establishment. Test compounds can be evaluated either by dosing one day after tumor cell implantation (inhibition regimen) or after tumors have reached a certain size (treatment regimen). Compounds are administered either intraperitoneally or orally in a vehicle of 1% tween-80 in saline each day. Tumor size is evaluated every three or seven days.

Colon cancer. The ability to treat or inhibit colon cancer can be evaluated in the test procedure of Smirnoff [Oncology Research 11: 255–64 (1999)].

Evaluation of Neuroprotection in Two in vivo Test Procedures

Transient global ischemia in the Mongolian gerbil. The effect of test compounds on preventing or treating brain injury in response to oxygen deprivation/reperfusion can be measured using the following test procedure.

Female Mongolian gerbils (60–80 g; Charles River Laboratories, Kingston, N.Y.) are housed in the Wyeth-Ayerst animal care facility (AAALAC certified) with a 12-hour light, 12-hour dark photoperiod and free access to tap water and a low-estrogen casein diet (Purina; Richmond, Ind.). After acclimation (3–5 days), gerbils are anesthetized with isoflurane (2–3% mixture with $O_2$), ovariectomized (Day 0). Beginning the following morning (Day 1), gerbils are treated subcutaneously each day with either vehicle (10% ETOH/corn oil), 17β-estradiol (1 mg/kg, sc) or an experimental compound. On Day 6, gerbils (n=4–5/group) are anesthetized with isoflurane, the common carotid arteries visualized via a mid-line neck incision and both arteries simultaneously occluded for 5 minutes with non-traumatic micro aneurysm clips. After occlusion, the clips are removed to allow cerebral reperfusion and the neck incision closed with wound clips. All animals are fasted overnight prior to the global ischemia surgery, a step that facilitates consistent ischemic injury. On Day 12, gerbils are exposed to a lethal dose of $CO_2$, and the brains frozen on dry ice and stored at −80° C.

The degree of neuronal protection is evaluated by in situ hybridization analysis of neurogranin mRNA. Briefly, 20 μm coronal cryostat sections are collected on gelatin-coated slides, dried and stored at −80° C. At the time of processing, the desiccated slide boxes are warmed to room temperature, the slides postfixed in 4% paraformaldehyde, treated with acetic anhydride and then delipidated and dehydrated with chloroform and ethanol. Processed section-mounted slides are then hybridized with 200 μl ($6 \times 10^6$ DPM/slide) of an antisense or sense (control) riboprobe for Neurogranin ($^{35}$S-UTP-labeled NG-241; bases 99–340). in a 50% formamide hybridization mix and incubated overnight at 55° C. in a humidified slide chamber without coverslipping. The following morning, the slides are collected in racks, immersed in 2×SSC (0.3 M NaCl, 0.03 M sodium citrate; pH 7.0)/10 mM DTT, treated with RNase A (20 μg/ml) and washed (2×30 min) at 67° C. in 0.1×SSC to remove nonspecific label. After dehydration, the slides are opposed to BioMax (BMR-1; Kodak) X-ray film overnight.

The level of neurogranin hybridization signal is used to quantitatively assess the degree of neuronal loss in the CA1 region after injury and to evaluate the efficacy of 17β-estradiol and experimental compounds. Neurogranin mRNA is selected for these studies because it is highly expressed in the hippocampal neurons including CA1, but absent in glia and other cell types present in this brain region. Therefore, measurement of the amount of neurogranin mRNA present represents surviving neurons. Relative optical density measurements of neurogranin hybridization signal are obtained from film autoradiograms with a computer based image analysis system (C-Imaging Inc., Pittsburgh, Pa.). The results from 6 sections (40 μm apart) per animal are averaged and statistically evaluated. Numerical values are reported as the mean±SEM. One-way analysis of variance is used to test for differences in the level of neurogranin mRNA and all statements of non-difference in the results section imply that $p>0.05$.

Middle cerebral artery occlusion in mice. Neuroprotection can be evaluated according to the test procedures described by Dubal [see, Dubal, et al., Proceedings of the National Academy of Sciences of the United States of America 98: 1952–1957 (2001), Dubal, et al., Journal of Neuroscience 19: 6385–6393 (1999)].

Ovulation Inhibition Standard Pharmacological Test Procedure

The test procedure is used to determine whether test compounds can inhibit or change the timing of ovulation. It can also be used to determine the number of oocytes ovulated [Lundeen, et al., J Steroid Biochem Mol Biol 78: 137–143 (2001)].

Based on the results obtained in the standard pharmacological test procedures, the compounds of this invention are estrogen receptor modulators useful in the treatment or inhibition of conditions, disorders, or disease states that are at least partially mediated by an estrogen deficiency or excess, or which may be treated or inhibited through the use of an estrogenic agent. The compounds of this invention are particularly useful in treating a peri-menopausal, menopausal, or postmenopausal patient in which the levels of endogenous estrogens produced are greatly diminished. Menopause is generally defined as the last natural menstrual period and is characterized by the cessation of ovarian function, leading to the substantial diminution of circulating estrogen in the bloodstream. As used herein, menopause also includes conditions of decreased estrogen production that may be surgically, chemically, or be caused by a disease state which leads to premature diminution or cessation of ovarian function.

The compounds of this invention are also useful in inhibiting or treating other effects of estrogen deprivation including, hot flushes, vaginal or vulvar atrophy, atrophic vaginitis, vaginal dryness, pruritus, dyspareunia, dysuria, frequent urination, urinary incontinence, urinary tract infections. Other reproductive tract uses include the treatment or inhibition of dysfunctional uterine bleeding. The compounds are also useful in treating or inhibiting endometriosis.

The compounds of this invention are also active in the brain and are therefore useful for inhibiting or treating Alzheimer's disease, cognitive decline, decreased libido, senile dementia, neurodegenerative disorders, depression, anxiety, insomnia, schizophrenia, and infertility. The compounds of this invention are also useful in treating or inhibiting benign or malignant abnormal tissue growth including, glomerulosclerosis, prostatic hypertrophy, uterine leiomyomas, breast cancer, scleroderma, fibromatosis, endometrial cancer, polycystic ovary syndrome, endometrial polyps, benign breast disease, adenomyosis, ovarian cancer, melanoma, prostate cancer, cancers of the colon, CNS cancers, such as glioma or astioblastomia.

The compounds of this invention are cardioprotective and are antioxidants, and are useful in lowering cholesterol, triglycerides, Lp(a), and LDL levels; inhibiting or treating hypercholesteremia, hyperlipidemia, cardiovascular disease, atherosclerosis, peripheral vascular disease, restenosis, and vasospasm, and inhibiting vascular wall damage from cellular events leading toward immune mediated vascular damage. The compounds of this invention are also useful in treating disorders associated with inflammation or autoimmune diseases, including inflammatory bowel disease (Crohn's disease, ulcerative colitis, indeterminate colitis), arthritis (rheumatoid arthritis, spondyloarthropathies, osteoarthritis), pleurisy, ischemia/reperfusion injury (e.g. stroke, transplant rejection, myocardial infarction, etc.), asthma, giant cell arteritis, prostatitis interstitial cystitis, uveitis, psoriasis, multiple sclerosis, systemic lupus erythematosus and sepsis.

The compounds of this invention are also useful in treating or inhibiting ocular disorders including cataracts, uveitis, and macular degeneration and in treating skin conditions such as aging, alopecia, and acne.

The compounds of this invention are also useful in treating or inhibiting metabolic disorders such as type-II diabetes, of lipid metabolism, appetite (e.g. anorexia nervosa and bulimia).

Compounds in this invention are also useful in treating or inhibiting bleeding disorders such as hereditary hemorrhagic telangiectasia, dysfunctional uterine bleeding, and combating hemorrhagic shock.

The compounds of this invention are useful in disease states where amenorrhea is advantageous, such as leukemia, endometrial ablations, chronic renal or hepatic disease or coagulation diseases or disorders.

The compounds of this invention can be used as a contraceptive agent, particularly when combined with a progestin.

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. Effective administration of the compounds of this invention may be given at an oral dose of from about 0.1 mg/day to about 1,000 mg/day. Preferably, administration will be from about 10 mg/day to about 600 mg/day, more preferably from about 50 mg/day to about 600 mg/day, in a single dose or in two or more divided doses. The projected daily dosages are expected to vary with route of administration.

Such doses may be administered in any manner useful in directing the active compounds herein to the recipient's bloodstream, including orally, via implants, parentally (including intravenous, intraperitoneal, intraarticularly and subcutaneous injections), rectally, intranasally, topically, ocularly (via eye drops), vaginally, and transdermally.

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidol silicon dioxide, phosphates, sodium dodecylsulfate, magnesium aluminum silicate, and triethanolamine. Oral formulations herein may utilize standard delay or time release formulations to alter the absorption of the active compound (s). The oral formulation may also consist of administering the active ingredient in water or a fruit juice, containing appropriate solubilizers or emulsifiers as needed.

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The preparation of representative examples of this invention is described below.

EXAMPLE 1

3-Amino-5-hydroxy-2-(4-hydroxyphenyl)-1H-inden-1-one

Step a) 3-Amino-5-methoxy-2-(4-methoxyphenyl)-1H-inden-1-one.

A mixture of methyl 4-methoxybenzoate (1.47 g, 7.47 mmole) and 4-methoxy phenylacetonitrile (1.00 g, 6.79 mmole) in dry THF (15 mL) was slowly added to 20 ml of 2.0 M of LDA at −10° C. The mixture was gradually allowed to warm to room temperature and left to stir overnight. The reaction was quenched with water and most of the THF was removed via vacuum. The crude aminoindenone was then filtered, dried and recrystallized from isopropanol to give a red orange solid (65% yield, m.p. 213° C.); MS m/e 281 (M+)$^+$.

Analysis for: $C_{17}H_{15}NO_3$
Calc'd: C, 72.58; H, 5.37; N, 4.98
Found: C, 71.7; H, 5.21; N, 4.87
Ref: Tetrahedron Lett. Vol.38, No 47 pp 8121–8124, (1997).

Step b) 3-Amino-5-hydroxy-2-(4-hydroxyphenyl)-1H-inden-1-one.

Boron tribromide (0.5 mL, 5.3 mmol) was added dropwise into a cold (−78° C.) mixture of 3-Amino-5-methoxy-2-(4-methoxyphenyl)-1H-inden-1-one (250 mg, 0.89 mmol), and dichloromethane (2.0 mL). The reaction mixture was allowed to come gradually to room temperature and stirred for 1 hour. The mixture was poured onto ice containing ammonium hydroxide (1 mL) and extracted with ethyl acetate. The organic extracts were washed with brine and were dried over $MgSO_4$. Evaporation and flash chromatography (5%–10% ETOH/dichloromethane) gave (126 mg, 56% yield) of the product as a purple solid: mp 260–265° C.;

MS m/e 254 (M+H)$^+$.
Analysis for: $C_{15}H_{11}NO_3 \times 0.5H_2O$
Calc'd: C, 68.70; H, 4.61; N, 5.39
Found: C, 68.14; H, 4.6; N, 4.98

EXAMPLE 2

5-Hydroxy-2-(4-hydroxyphenyl)-1H-indene-1,3(2H)-dione

Step a) 5-methoxy-2-(4-methoxyphenyl)-1H-inden-1,3(2H)-dione.
3-Amino-5-methoxy-2-(4-methoxyphenyl)-1H-inden-1-one (500 mg, 1.78 mmol), was suspended in a solution of 20% $H_2SO_4$ and heated to 120° for 1 h. The reaction was allowed to cool and the residual solid filtered and the filter cake was washed copiously with water and dried in vacuo to give a light white solid (0.5 g, 99% yield, m.p. 163° C.);
MS m/e 281 (M−H)$^+$
Analysis for: $C_{17}H_{14}O_4$
Calc'd: C, 72.33; H, 5.00; N, 0.00
Found: C, 72.20; H, 4.93; N, 0.06

Step b) 5-Hydroxy-2-(4-hydroxyphenyl)-1H-indene-1,3(2H)-dione.
Pyridine hydrochloride (400 mg) was heated to 190° C. To the melt was added 5-methoxy-2-(4-methoxyphenyl)-1H-inden-1,3(2H)-dione (150 mg, 0.53 mmol) and the reaction was stirred for 3 h. The mixture was cooled to room temperature and dissolved in water and extracted with ethyl acetate. The organic layers were combined and washed with 1 N HCl, water then brine and dried over $MgSO_4$. Evaporation and flash chromatography (50%–60% EtOAc/petroleum ether) gave the product as a light brown solid, (81 mg, 60% yield, m.p. 227–228° C.); MS m/e 255 (M+H)$^+$.
Analysis for: $C_{15}H_{10}O_4$
Calc'd: C, 70.86; H, 3.96; N, 0.00
Found: C, 70.19; H, 3.92; N, 0.08

EXAMPLE 3

3-Bromo-6-hydroxy-2-(4-hydroxyphenyl)-1H-inden-1-one

Step a) 3-Bromo-6-methoxy-2-(4-methoxyphenyl)-1H-inden-1-one and 3-Bromo-5-methoxy-2-(4-methoxyphenyl)-1H-inden-1-one.

A mixture of 5-methoxy-2-(4-methoxyphenyl)-1H-inden-1,3(2H)-dione (500 mg, 1.77 mmol), and triphenylphosphine (696 mg, 1.95 mmole) was suspended in anhydrous chloroform (10 mL) and heated to 45°. Carbon tetrabromide (646 mg, 1.95 mmol) dissolved in chloroform (2 mL) was added over 15 minutes and the reaction was allowed to stir for 4 h.

The reaction was allowed to cool and the residual solid filtered and washed with EtOAc. The volatiles were removed under vacuum and the residue was purified by flash chromatography (10–20% EtOAc/petroleum ether) to give a partially separable mixture of 3-Bromo-6-methoxy-2-(4-methoxyphenyl)-1H-inden-1-one (red solid, mg, m.p. 152° C.; MS m/e 344 (M)$^+$) and 3-Bromo-5-methoxy-2-(4-methoxyphenyl)-1H-inden-1-one (orange solid, 0.5 mg, m.p. 142° C.); MS m/e 344 (M)$^+$
Analysis for: $C_{17}H_{13}BrO_3$
Calc'd: C, 59.15; H, 3.8; N, 0.00
Found: C, 58.94; H, 3.58; N, 0.06

Step b) 3-Bromo-6-hydroxy-2-(4-hydroxyphenyl)-1H-inden-1-one.
The title compound was prepared in substantially the same manner as described in Example 1, step b and was obtained as a purple solid, m.p. 240° C. decomposed; MS m/e 334 (M+NH$_4$)$^+$.
Analysis for: $C_{15}H_9BrO_3 \times 0.5H_2O$
Calc'd: C, 55.24; H, 3.09; N, 0.00
Found: C, 55.29; H, 3.05; N, 0.00

EXAMPLE 4

3-Bromo-5-hydroxy-2-(4-hydroxyphenyl)-1H-inden-1-one

The title compound was prepared in substantially the same manner as described in Example 1, step b and was obtained as a dark red solid, m.p. 245° C. decomposed; MS m/e 334 (M+NH$_4$)$^+$.

Analysis for: $C_{15}H_9BrO_3$
Calc'd: C, 56.81; H, 2.86; N, 0.00
Found: C, 56.41; H, 2.75; N, 0.06

EXAMPLE 5

3-(Ethylamino)-6-hydroxy-2-(4-hydroxyphenyl)-1H-inden-1-one

Step a) 3-(Ethylamino-6-methoxy-2-(4-methoxyphenyl)-1H-inden-1-one

A mixture of 3-Bromo-6-methoxy-2-(4-methoxyphenyl)-1H-inden-1-one (150 mg, 0.4345 mmol), ethyl amine (0.06 mL, 1.09 mmol), and triethyl amine (0.5 ml) in N,N, dimethyl formamide (3 mL) was heated at 60° C. for 4 h. The reaction was cooled to room temperature and poured into water. The residual product was filtered and washed with water and purified by flash chromatography (50% ethyl acetate/petroleum ether) to give the product as a orange solid, which was used directly in the next reaction.

Step b) 3-(Ethylamino)-6-methoxy-2-(4-methoxyphenyl)-1H-inden-1-one

The title compound was prepared in substantially the same manner as described in Example 1, step b and was obtained as a dark red solid, m.p. 250° C. decomposed; MS m/e 282 (M+H)$^+$.

Analysis for: $C_{17}H_{15}NO_3 \times 0.5H_2O$
Calc'd: C, 70.33; H, 5.56; N, 4.82
Found: C, 70.67; H, 5.45; N, 4.43

EXAMPLE 6

3-(Ethylthio)-6-hydroxy-2-(4-hydroxyphenyl)-1H-inden-1-one

Step a) 3-(Ethylamino)-6-methoxy-2-(4-methoxyphenyl)-1H-inden-1-one

A mixture of 3-Bromo-6-methoxy-2-(4-methoxyphenyl)-1H-inden-1-one (150 mg, 0.4345 mmol), sodium ethanethiolate (91.4 mg, 1.09 mmol), and triethyl amine (0.5 ml) in N,N, dimethyl formamide (3 mL) was heated at 80° C. for 24 h. The reaction was cooled to room temperature was poured into water and extracted with ethyl acetate. The organic extracts were washed with brine and were dried over MgSO$_4$. Evaporation and flash chromatography (10% ethyl acetate/petroleum ether) gave (126 mg, 89% yield) of the product as a dark red solid: mp 88–90° C.; MS m/e 327 (M+H)$^+$.

Analysis for: $C_{19}H_{18}O_3$ S
Calc'd: C, 69.91; H, 5.56; N, 0.00
Found: C, 69.95H, 5.66; N, 0.04

Step b) 3-(Ethylthio)-6-hydroxy-2-(4-hydroxyphenyl)-1H-inden-1-one

The title compound was prepared in substantially the same manner as described in Example 1, step b and was obtained as a dark red solid, m.p. 78–81° C.; MS m/e 299 (M+H)$^+$.

Analysis for: $C_{17}H_{14}O_3S \times 1.0H_2O$
Calc'd: C, 64.54; H, 5.10; N, 0.00
Found: C, 64.92; H, 5.10; N, 0.43

EXAMPLE 7

3-(Ethylthio)-5-hydroxy-2-(4-hydroxyphenyl)-1H-inden-1-one

Step a) 3-(Ethylamino)-5-methoxy-2-(4-methoxyphenyl)-1H-inden-1-one

The title compound was prepared in substantially the same manner as described in Example 6, step a and was obtained as an orange red solid, m.p. 100–102° C.; MS m/e 326 (M+)$^+$.

Analysis for: $C_{19}H_{18}O_3S$
Calc'd: C, 69.91; H, 5.56; N, 0.00
Found: C, 68.06; H, 5.1; N, 0.04

Step b) 3-(Ethylthio)-5-hydroxy-2-(4-hydroxyphenyl)-1H-inden-1-one

The title compound was prepared in substantially the same manner as described in Example 1, step b and was obtained as a dark purple solid, m.p. 118–120° C.; MS m/e 299 (M+H)$^+$.

Analysis for: $C_{17}H_{14}O_3S \times 0.5H_2O$
Calc'd: C, 66.43; H, 4.92; N, 0.00
Found: C, 67.04; H, 4.92; N, 0.43

EXAMPLE 8

6-hydroxy-2-(4-hydroxyphenyl)-3-(methylthio)-1H-inden-1-one

Step a) 6-methoxy-2-(4-methoxyphenyl)-3-(methylthio)-1H-inden-1-one

The title compound was prepared in substantially the same manner as described in Example 6, step a and was obtained as a red solid, m.p. 123–125° C.; MS m/e 312 (M+)$^+$.

Analysis for: $C_{18}H_{16}O_3S$
Calc'd: C, 69.21; H, 5.16; N, 0.00
Found: C, 68.69; H, 5.32; N, 0.00

Step b) 6-hydroxy-2-(4-hydroxyphenyl)-3-(methylthio)-1H-inden-1-one

The title compound was prepared in substantially the same manner as described in Example 1, step b and was obtained as a dark purple solid, m.p. 90–92° C.; MS m/e 283 (M–H)$^+$.

Analysis for: $C_{16}H_{12}O_3S \times 0.75H_2O$
Calc'd: C, 64.52; H, 4.57; N, 0.00
Found: C, 64.34; H, 4.48; N, 0.20

EXAMPLE 9

5-hydroxy-2-(4-hydroxyphenyl)-3-(methylthio)-1H-inden-1-one

Step a) 5-methoxy-2-(4-methoxyphenyl)-3-(methylthio)-1H-inden-1-one

The title compound was prepared in substantially the same manner as described in Example 6, step a and was obtained as a red solid, m.p. 108–110° C.; MS m/e 312 (M)$^+$.

Analysis for: $C_{18}H_{16}O_3S$
Calc'd: C, 69.21; H, 5.16; N, 0.00
Found: C, 68.32; H, 5.07; N, 0.00

Step b) 5-hydroxy-2-(4-hydroxyphenyl)-3-(methylthio)-1H-inden-1-one

The title compound was prepared in substantially the same manner as described in Example 1, step b and was obtained as a dark purple solid, m.p. 183–185° C.; MS m/e 285 (M+H)$^+$.

Analysis for: $C_{16}H_{12}O_3S \times 0.75H_2O$
Calc'd: C, 64.52; H, 4.57; N, 0.00
Found: C, 64.80; H, 4.54; N, 0.01

EXAMPLE 10

6-hydroxy-2-(4-hydroxyphenyl)-3-phenyl-1H-inden-1-one

Step a) 3-hydroxy-6-methoxy-2-(4-methoxyphenyl)-3-phenyl-indan-1-one and 3-hydroxy-5-methoxy-2-(4-methoxyphenyl)-3-phenyl-indan-1-one Sodium bis(trimethylsilyl) amide (0.6 N, 7.09 mL, 4.25 mmol) was added dropwise into a cold (0° C.) mixture of 5-methoxy-2-(4-methoxyphenyl)-1H-inden-1,3(2H)-dione (1000 mg, 3.54 mmol) and tetrahydrofuran (15 mL). The mixture was allowed to stir for 1.0 h. Phenyl lithium (4.13 mL, 7.44 mmol) was added dropwise into the mixture at 0° C. The reaction mixture was allowed to warm to RT and stirred for 2 h. The reaction was quenched with 2 N HCl, poured into water, and extracted with ethyl acetate. The organic extracts were washed with brine and dried over MgSO$_4$. Evaporation and flash chromatography (30%–50% ethyl acetate/petroleum ether) gave 3-hydroxy-6-methoxy-2-(4-methoxyphenyl)-3-phenyl-indan-1-one as a light red foam and 3-hydroxy-5-methoxy-2-(4-methoxyphenyl)-3-phenyl-indan-1-one as a light orange solid: mp 68–70; MS m/e 361 (M+H)$^+$.

Analysis for: $C_{23}H_{20}O_4$
Calc'd: C, 74.78; H, 5.73; N, 0.00
Found: C, 74.62; H, 5.67; N, 0.05

Step b) 6-hydroxy-2-(4-hydroxyphenyl)-3-phenyl-1H-inden-1-one

The title compound was prepared in substantially the same manner as described in Example 2, step b and was obtained as a purple solid, m.p. 100–110° C.; MS m/e 315 (M+H)$^+$.

Analysis for: $C_{21}H_{14}O_3$
Calc'd: C, 80.24; H, 4.49; N, 0.00
Found: C, 76.78; H, 4.41; N, 0.13

EXAMPLE 11

5-hydroxy-2-(4-hydroxyphenyl)-3-phenyl-1H-inden-1-one

The title compound was prepared in substantially the same manner as described in Example 2, step b and was obtained as a red solid, m.p. 222–225° C.; MS m/e 315 (M+H)$^+$.

Analysis for: $C_2,H_{14}NO_3$
Calc'd: C, 80.24; H, 4.49; N, 0.00
Found: C, 80.28; H, 4.35; N, 0.36

EXAMPLE 12

6-hydroxy-2-(4-hydroxyphenyl)-3-methyl-1H-inden-1-one

Step a) 3-hydroxy-6-methoxy-2-(4-methoxyphenyl)-3-methyl-indan-1-one

The title compound was prepared in substantially the same manner as described in Example 10, step a, and was obtained as a white solid, m.p. 125–129° C.; MS m/e 299 (M+H)$^+$.

Analysis for: $C_{18}H_{18}O_4 \times 0.25H_2O$
Calc'd: C, 71.39; H, 6.16; N, 0.00
Found: C, 71.55; H, 6.23; N, 0.00

Step b) 6-hydroxy-2-(4-hydroxyphenyl)-3-methyl-1H-inden-1-one

The title compound was prepared in substantially the same manner as described in Example 2, step b and was obtained as a red solid, m.p. 240–245° C.; MS m/e 253 (M+H)$^+$.

Analysis for: $C_{16}H_{12}O_3 \times 0.25H_2O$
Calc'd: C, 74.84; H, 4.91; N, 0.00
Found: C, 75.22; H, 4.78; N, 0.02

EXAMPLE 13

5-hydroxy-2-(4-hydroxyphenyl)-3-methyl-1H-inden-1-one

Step a) 3-hydroxy-6-methoxy-2-(4-methoxyphenyl)-3-methyl-indan-1-one

The title compound was prepared in substantially the same manner as described in Example 10, step a, and was obtained as a white solid, m.p. 138–146° C.; MS m/e 299 (M+H)$^+$.

Analysis for: $C_{18}H_{18}O_4 \times 0.25H_2O$
Calc'd: C, 72.47; H, 6.08; N, 0.00
Found: C, 71.94; H, 6.08; N, 0.00

Step b) 5-hydroxy-2-(4-hydroxyphenyl)-3-methyl-1H-inden-1-one

The title compound was prepared in substantially the same manner as described in Example 2, step b and was obtained as a red solid, m.p. 251° C.; MS m/e 253 (M+H)$^+$.

Analysis for: $C_{16}H_{12}O_3 \times 0.25H_2O$
Calc'd: C, 76.18; H, 4.79; N, 0.00
Found: C, 75.78; H, 4.74; N, 0.00

EXAMPLE 14

4,6-dihydroxy-2-(4-hydroxyphenyl)-1H-inden-1,3(2H)-dione

Step a) 3-Amino-5,7-dimethoxy-2-(4-methoxyphenyl)-1H-inden-1-one.

The title compound was prepared in substantially the same manner as described in Example 1, step a and was obtained as a red brown solid, m.p. 220° C. decomposed; MS m/e 311 (M+)$^+$.

Analysis for: $C_{18}H_{17}NO_4$
Calc'd: C, 69.44; H, 5.50; N, 4.50
Found: C, 68.65; H, 5.50; N, 4.22

Step b) 4,6-dimethoxy-2-(4-methoxyphenyl)-1H-inden-1,3(2H)-dione

The title compound was prepared in substantially the same manner as described in Example 2, step a and was obtained as a tan solid, m.p. 180° C.; MS m/e 313 (M+H)$^+$.

Analysis for: $C_{18}H_{16}O_5$
Calc'd: C, 69.22; H, 5.16; N, 0.00
Found: C, 69.38; H, 5.21; N, 0.10

Step c) 4,6-dihydroxy-2-(4-hydroxyphenyl)-1H-inden-1,3(2H)-dione

The title compound was prepared in substantially the same manner as described in Example 2, step b and was obtained as a tan solid, m.p. 220–222° C.; MS m/e 270 (M+)$^+$.

Analysis for: $C_{15}H_{10}O_5$
Calc'd: C, 66.67; H, 3.73; N, 0.00
Found: C, 63.71; H, 3.49; N, 0.08

EXAMPLE 15

3-bromo-4,6-dihydroxy-2-(4-hydroxyphenyl)-1H-inden-1-one

Step a) 3-bromo-4,6-dimethoxy-2-(4-methoxyphenyl)-1H-inden-1-one

The title compound was prepared in substantially the same manner as described in Example 3, step a and was obtained as a purple solid, m.p. 160–162° C.; MS m/e 375 (M+H)$^+$.

Analysis for: $C_{18}H_{15}BrO_4$
Calc'd: C, 57.62; H, 4.53; N, 0.00
Found: C, 57.51; H, 4.87; N, 0.04

Step b) 3-bromo-4,6-dihydroxy-2-(4-hydroxyphenyl)-1H-inden-1-one

The title compound was prepared in substantially the same manner as described in Example 1, step b and was obtained as a purple solid, m.p. 350° C. decomposed; MS m/e 333 (M+)$^+$.

Analysis for: $C_{15}H_9BrO_4 \times 1.25H_2O$
Calc'd: C, 50.66; H, 3.26; N, 0.00
Found: C, 50.78; H, 3.17; N, 0.00

EXAMPLE 16

3-bromo-6-hydroxy-2-(4-hydroxyphenyl)-4-methoxy-1H-inden-1-one

The title compound was prepared in substantially the same manner as described in Example 1, step b and was obtained as a purple solid, m.p. 210° C. decomposed; MS m/e 346 (M–H)$^+$.

Analysis for: $C_{16}H_{11}BrO_4$
Calc'd: C, 55.36; H, 3.19; N, 0.00
Found: C, 54.81; H, 3.36; N, 0.17

EXAMPLE 17

5,7-Dihydroxy-2-(4-hydroxyphenyl)-3-methyl-1H-inden-1-one

Step a) 5,7-Dimethoxy-2-(4-methoxyphenyl)-3-methyl-1H-inden-1-one

The title compound was prepared in substantially the same manner as described in Example 10, step a and was obtained as a orange solid, m.p. 126–129° C.; MS m/e 310 (M–)$^+$.

Analysis for: $C_{19}H_{18}O_4$
Calc'd: C, 73.53; H, 5.85; N, 0.00
Found: C, 70.83; H, 5.18; N, 0.07

Step b) 5,7-Dihydroxy-2-(4-hydroxyphenyl)-3-methyl-1H-inden-1-one

The title compound was prepared in substantially the same manner as described in Example 2, step b and was obtained as a purple solid, m.p. 215–217° C.; MS m/e 267 (M–H)$^+$.

Analysis for: $C_{16}H_{12}O_4 \times 1.00H_2O$
Calc'd: C, 67.13; H, 4.89; N, 0.00
Found: C, 67.65; H, 4.78; N, 0.07

EXAMPLE 18

4,6-Dihydroxy-2-(4-hydroxyphenyl)-3-(methylthio)-1H-inden-1-one

Step a) 4,6-dimethoxy-2-(4-methoxyphenyl)-3-(methylthio)-1H-inden-1-one

The title compound was prepared in substantially the same manner as described in Example 6, step a and was obtained as a purple solid, m.p. 120–123° C.; MS m/e 343 (M+H)$^+$.

Analysis for: $C_{19}H_{18}O_4S$
Calc'd: C, 66.65; H, 5.30; N, 0.00
Found: C, 66.27; H, 5.11; N, 0.08

Step b) 4,6-Dihydroxy-2-(4-hydroxyphenyl)-3-(methylthio)-1H-inden-1-one

The title compound was prepared in substantially the same manner as described in Example 1, step b and was obtained as a purple solid, m.p. 208–210° C.; MS m/e 299 (M–H)$^+$.

Analysis for: $C_{16}H_{12}O_4S \times 1.25H_2O$
Calc'd: C, 59.53; H, 4.53; N, 0.00
Found: C, 59.28; H, 4.62; N, 0.6

EXAMPLE 19

3-(Ethylthio)-4,6-Dihydroxy-2-(4-hydroxyphenyl)-1H-inden-1-one

Step a) 3-(ethylthio)-4,6-dimethoxy-2-(4-methoxyphenyl)-1H-inden-1-one

The title compound was prepared in substantially the same manner as described in Example 6, step a and was obtained as a purple solid, m.p. 75–77° C.; MS m/e 357 (M+H)$^+$.

Analysis for: $C_{20}H_{20}O_4S$
Calc'd: C, 67.39; H, 5.66; N, 0.00
Found: C, 67.11; H, 5.84; N, 0.12

Step b) 3-(Ethylthio)-4,6-Dihydroxy-2-(4-hydroxyphenyl)-1H-inden-1-one

The title compound was prepared in substantially the same manner as described in Example 1, step b and was obtained as a red solid, m.p. 187–190° C.; MS m/e 315 (M+H)$^+$.

Analysis for: $C_{17}H_{14}O_4S$
Calc'd: C, 64.95; H, 4.49; N, 0.00
Found: C, 58.52; H, 4.35; N, 0.09

EXAMPLE 20

4,6-Dihydroxy-2-(4-hydroxyphenyl)-3-phenyl-1H-inden-1-one

The title compound was prepared in substantially the same manner as described in Example 10, step a and b, and was obtained as a purple solid, m.p. 223–225° C.; MS m/e 331 (M+H)$^+$.

Analysis for: $C_{21}H_{14}O_4$
Calc'd: C, 76.36; H, 4.27; N, 0.00
Found: C, 71.95; H, 4.31; N, 0.10

EXAMPLE 21

5,7-Dihydroxy-2-(4-hydroxyphenyl)-3-phenyl-1H-inden-1-one

The title compound was prepared in substantially the same manner as described in Example 10, step a and b, and was obtained as a purple solid, m.p. 128–130° C.; MS m/e 331 (M+H)$^+$.

Analysis for: $C_{21}H_{14}O_4 \times 1.5H_2O$
Calc'd: C, 70.59; H, 4.80; N, 0.00
Found: C, 70.20; H, 4.54; N, 0.24

EXAMPLE 22

5,6-Dihydroxy-2-(4-hydroxyphenyl)-3-methyl-1H-inden-1-one

The title compound was prepared in substantially the same manner as described in Example 1, step a, Example 2, step a, Example 10 steps a and b, to give a purple solid, m.p. 226–229° C.; MS m/e 269 (M+H)$^+$.

Analysis for: $C_{16}H_{12}O_4 \times 0.25H_2O$
Calc'd: C, 70.45; H, 4.62; N, 0.00
Found: C, 70.20; H, 4.76; N, 0.02

---

What is claimed is:

1. A compound of formula I having the structure,

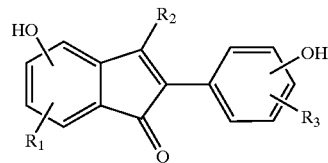

I wherein, $R_1$ is hydrogen, hydroxyl, halogen, trifluoroalkyl of 1–6 carbon atoms, alkyl of 1–6 carbon atoms, cycloalkyl of 3–8 carbon atoms, alkenyl of 2–7 carbon atoms, alkoxy of 1–6 carbon atoms, trifluoroalkoxy of 1–6 carbon atoms, thioalkyl of 1–6 carbon atoms, sulfoxoalkyl of 1–6 carbon atoms, sulfonoalkyl of 1–6 carbon atoms, sulfoxoalkyl of 1–6 carbon atoms, sulfonoalkyl of 1–6 carbon atoms, —CN, —NO$_2$, —CHFCN, —CF$_2$CN, aryl of 6–10 carbon atoms, —NR$_4$R$_5$, —NCOR$_4$, —SR$_4$, —SOR$_4$, —SO$_2$R$_4$, or a 5 or 6-membered heterocyclic ring having 1 to 4 heteroatoms selected from O, N or S; wherein the alkyl or alkenyl moieties are optionally substituted with hydroxyl, —CN, halogen, trifluoroalkyl of 1–6 carbon atoms, trifluoroalkoxy of 1–6 carbon atoms, —COR$_4$, —CO$_2$R$_4$, —CONR$_4$R$_5$, or NR$_4$R$_5$;

$R_2$ is hydrogen, hydroxyl, alkyl of 1–6 carbon atoms, halogen, phenyl substituted with one of hydrogen, hydroxyl, halogen, trifluoroalkyl of 1–6 carbon atoms, alkyl of 1–6 carbon atoms, cycloalkyl of 3–8 carbon atoms, alkenyl of 2–7 carbon atoms, alkoxy of 1–6 carbon atoms, trifluoroalkoxy of 1–6 carbon atoms, thioalkyl of 1–6 carbon atoms, sulfoxoalkyl of 1–6 carbon atoms, sulfonoalkyl of 1–6 carbon atoms, sulfoxoalkyl of 1–6 carbon atoms, sulfonoalkyl of 1–6 carbon atoms, —CN, —NO$_2$, —CHFCN, —CF$_2$CN, aryl of 6–10 carbon atoms, —NR$_4$R$_5$, —NCOR$_4$, —SR$_4$, —SOR$_4$, —SO$_2$R$_4$, or a 5 or 6-membered heterocyclic ring having 1 to 4 heteroatoms selected from O, N or S; wherein the alkyl or alkenyl moieties are optionally sustituted with hydroxyl, —CN, halogen, trifluoroalkyl of 1–6 carbon atoms, trifluoroalkoxy of 1–6 carbon atoms, —COR$_4$, —CO$_2$R$_4$, —CONR$_4$R$_5$, or NR$_4$R$_5$, provided that when $R_1=R_3=H$, $R_2$ is not hydroxy phenyl, alkylthio of 1–6 carbon atoms, thioalkyl of 1–6 carbon atoms, amino, aminoalkyl of 1–6 carbon atoms, alkylamino of 1–6 carbon atoms, alkoxy of 1–6 carbon atoms, or alkenyl of 2–7 carbon atoms;

$R_3$ is hydrogen, halogen, hydroxyl, alkyl of 1–6 carbon atoms, alkoxy of 1–6 carbon atoms, trifluoroalkyl of 1–6 carbon atoms, or trifluoroalkoxy of 1–6 carbon atoms;

$R_4$ and $R_5$ are each, independently, hydrogen, alkyl of 1–6 carbon atoms, or aryl of 6–10 carbon atoms;

or a pharmaceutically acceptable salt thereof.

2. The compound according to claim 1, wherein $R_3$ is hydrogen.

3. The compound according to claim 2, wherein $R_1$ is hydrogen, hydroxyl, or alkoxy of 1–6 carbon atoms.

4. The compound according to claim 3, wherein $R_2$ is alkyl of 1–6 carbon atoms, hydroxyl, halogen, alkylamino of 1–6 carbon atoms, or alkylthio of 1–6 carbon atoms.

5. A compound selected from the group consisting of:

a) 3-amino-5-hydroxy-2-(4-hydroxyphenyl)-1H-inden-1-one;

b) 5-hydroxy-2-(4-hydroxyphenyl-1H-indene-1,3(2H)-dione;

c) 3bromo-6-hydroxy-2-(4-hydroxyphenyl)-1H-inden-1-one;

d) 3-bromo-5-hydroxy-2-(4-hydroxyphenyl)-1H-inden-1-one;

e) 3-(ethylamino)-6-hydroxy-2-(4-hydroxyphenyl)-1H-inden-1-one;

f) 3-(ehylthio)-6-hydroxy-2-(4-hydroxyphenyl)-1H-inden-1-one;

g) 3-(ethylthio)-5-hydroxy-2-(4-hydroxyphenyl)-1H-inden-1-one;

h) 6-hydroxy-2-(4-hydroxyphenyl)-3-(methylthio)-1H-inden-1-one;

i) 5-hydroxy-2-(4-hydroxyphenyl)-3-(methylthio)-1H-inden-1-one;

j) 6-hydroxy-2-(4-hydroxyphenyl)-3-phenyl-1H-inden-1-one;

k) 5-hydroxy-2-(4-hydroxyphenyl)-3-phenyl-1H-inden-1-one;

l) 6-hydroxy-2-(4-hydroxyphenyl)-3-methyl-1H-inden-1-one;

m) 5-hydroxy-2-(4-hydroxyphenyl)-3-methyl-1H-inden-1-one;

n) 4,6-dihydroxy-2-(4-hydroxyphenyl)-1H-inden-1,3(2H)-dione;

o) 3-bromo-4,6-dihydroxy-2-(4-hydroxyphenyl)-1H-inden-1-one;

p) 3-bromo-6-hydroxy-2-(4-hydroxyphenyl)-4-methoxy-1H-inden-1-one;

q) 5,7-dihydroxy-2-(4-hydroxyphenyl)-3-methyl-1H-inden-1-one;

r) 4,6dihydroxy-2-(4-hydroxyphenyl)-3-(methylthio)-1H-inden-1-one;

s) 3-(ethylthio)-4,6-dihydroxy-2-(4-hydroxyphenyl)-1H-inden-1-one;

t) 4,6-dihydroxy-2-(4-hydroxyphenyl)-3-phenyl-1H-inden-1-one;

u) 5,7-dihydroxy-2-(4-hydroxyphenyl)-3-phenyl-1H-inden-1-one;

v) 5,6-dihydroxy-2-(4-hydroxyphenyl)-3-methyl-1H-inden-1-one or a pharmaceutically acceptable salt thereof.

6. A method of treating or inhibiting prostatitis or interstitial cystitis in a mammal in need thereof, which comprises providing to said mammal an effective amount of a compound of formula I, having the structure

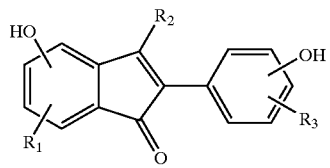

wherein, $R_1$ is hydrogen, hydroxyl, halogen, trifluoroalkyl of 1–6 carbon atoms, alkyl of 1–6 carbon atoms, cycloalkyl of 3–8 carbon atoms, alkenyl of 2–7 carbon atoms, alkoxy of 1–6 carbon atoms, trifluoroalkoxy of 1–6 carbon atoms, thioalkyl of 1–6 carbon atoms, sulfoxoalkyl of 1–6 carbon atoms, sulfonoalkyl of 1–6 carbon atoms, —CN, —NO$_2$, —CHFCN, —CF$_2$CN, aryl of 6–10 carbon atoms, —NR$_4$R$_5$, —NCOR$_4$, —SR$_4$, —SOR$_4$, —SO$_2$R$_4$, or a 5 or 6-membered heterocyclic ring having 1 to 4 heteroatoms selected from O, N or S; wherein the alkyl or alkenyl moieties are optionally substituted with hydroxyl, —CN, halogen, trifluroalkyl of 1–6 carbon atoms, trifluoroalkoxy of 1–6 carbon atoms, —COR$_4$, —CO$_2$R$_4$, —CONR$_4$R$_5$, or NR$_4$R$_5$;

$R_2$ is hydrogen, hydroxyl, alkyl of 1–6 carbon atoms, halogen, phenyl substituted with $R_1$, alkylthio of 1–6 carbon atoms, thioalkyl of 1–6 carbon atoms, amino, aminoalkyl of 1–6 carbon atoms, alkylamino of 1–6 carbon atoms, alkoxy of 1–6 carbon atoms, or alkenyl of 2–7 carbon atoms;

$R_3$ is hydrogen, halogen, hydroxyl, alkyl of 1–6 carbon atoms, alkoxy of 1–6 carbon atoms, trifluoroalkyl of 1–6 carbon atoms, or trifluoroalkoxy of 1–6 carbon atoms;

$R_4$ and $R_5$ are each, independently, hydrogen, alkyl of 1–6 carbon atoms, or aryl of 6–10 carbon atoms;

or a pharmaceutically acceptable salt thereof.

7. A method of treating or inhibiting inflammatory bowel disease, Crohn's disease, ulcerative proctitis, or colitis in a mammal in need thereof, which comprises providing to said mammal an effective amount of a compound of formula I, having the structure

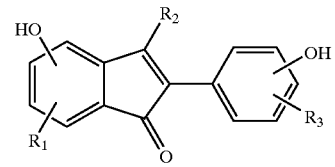

wherein, $R_1$ is hydrogen, hydroxyl, halogen, trifluoroalkyl of 1–6 carbon atoms, alkyl of 1–6 carbon atoms, cycloalkyl of 3–8 carbon atoms, alkenyl of 2–7 carbon atoms, alkoxy of 1–6 carbon atoms, trifluoroalkoxy of 1–6 carbon atoms, thioalkyl of 1–6 carbon atoms, sulfoxoalkyl of 1–6 carbon atoms, sulfonoalkyl of 1–6 carbon atoms, —CN, —NO$_2$, —CHFCN, —CF$_2$CN, aryl of 6–10 carbon atoms, —NR$_4$R$_5$, —NCOR$_4$, —SR$_4$, —SOR$_4$—SO$_2$R$_4$, or a 5 or 6-membered heterocyclic ring having 1 to 4 heteroatoms selected from O, N or S; wherein the alkyl or alkenyl moieties are optionally substituted with hydroxyl, —CN, halogen, trifluoroalkyl of 1–6 carbon atoms, trifluoroalkoxy of 1–6 carbon atoms, —COR$_4$, —CO$_2$R$_4$, —CONR$_4$R$_5$, or NR$_4$R$_5$;

$R_2$ is hydrogen, hydroxyl, alkyl of 1–6 carbon atoms, halogen, phenyl substituted with $R_1$, alkylthio of 1–6 carbon atoms, thioalkyl of 1–6 carbon atoms, amino, aminoalkyl of 1–6 carbon atoms, alkylamino of 1–6 carbon atoms, alkoxy of 1–6 carbon atoms, or alkenyl of 2–7 carbon atoms;

$R_3$ is hydrogen, halogen, hydroxyl, alkyl of 1–6 carbon atoms, alkoxy of 1–6 carbon atoms, trifluoroalkyl of 1–6 carbon atoms, or trifluoroalkoxy of 1–6 carbon atoms;

$R_4$ and $R_5$ are each, independently, hydrogen, alkyl of 1–6 carbon atoms, or aryl of 6–10 carbon atoms;

or a pharmaceutically acceptable salt thereof.

8. A method of treating or inhibiting prostatic hypertrophy, uterine leiomyomas, breast cancer, endometrial cancer, polycystic ovary syndrome, endometrial polyps, benign breast disease, adenomyosis, ovarian cancer, melanoma, prostrate cancer, colon cancer, glioma or astioblastomia in a mammal in need thereof, which comprises providing to said mammal an effective amount of a compound of formula I, having the structure

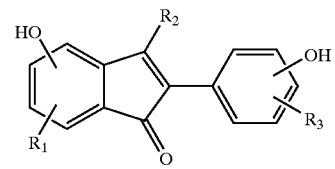

wherein, $R_1$ is hydrogen, hydroxyl, halogen, trifluoroalkyl of 1–6 carbon atoms, alkyl of 1–6 carbon atoms, cycloalkyl of 3–8 carbon atoms, alkenyl of 2–7 carbon atoms, alkoxy of 1–6 carbon atoms, trifluoroalkoxy of 1–6 carbon atoms, thioalkyl of 1–6 carbon atoms, sulfoxoalkyl of 1–6 carbon atoms, sulfonoalkyl of 1–6 carbon atoms, —CN, —NO$_2$, —CHFCN, —CF$_2$CN, aryl of 6–10 carbon atoms, —NR$_4$R$_5$, —NCOR$_4$, —SR$_4$, —SOR$_4$, —SO$_2$R$_4$, or a 5 or 6-membered heterocyclic ring having 1 to 4 heteroatoms selected from O, N or S; wherein the alkyl or alkenyl moieties are optionally substituted with hydroxyl, —CN, halogen, trifluoroalkyl of 1–6 carbon atoms, trifluoroalkoxy of 1–6 carbon atoms, —COR$_4$, —CO$_2$R$_4$, —CONR$_4$R$_5$, or NR$_4$R$_5$;

R$_2$ is hydrogen, hydroxyl, alkyl of 1–6 carbon atoms, halogen, phenyl substituted with R$_1$, alkylthio of 1–6 carbon atoms, thioalkyl of 1–6 carbon atoms, amino, aminoalkyl of 1–6 carbon atoms, alkylamino of 1–6 carbon atoms, alkoxy of 1–6 carbon atoms, or alkenyl of 2–7 carbon atoms;

R$_3$ is hydrogen, halogen, hydroxyl, alkyl of 1–6 carbon atoms, alkoxy of 1–6 carbon atoms, trifluoroalkyl of 1–6 carbon atoms, or trifluoroalkoxy of 1–6 carbon atoms;

R$_4$ and R$_5$ are each, independently, hydrogen, alkyl of 1–6 carbon atoms, or aryl of 6–10 carbon atoms;

or a pharmaceutically acceptable salt thereof.

9. A method of lowering cholesterol, triglycerides, Lp(a), or LDL levels; inhibiting or treating hypercholesteremia; hyperlipidemia; cardiovascular disease; atherosclerosis; hypertension; peripheral vascular disease; restenosis, or vasospasm; or inhibiting vascular wall damage from cellular events leading toward immune mediated vascular damage in a mammal in need thereof, which comprises providing to said mammal an effective amount of a compound of formula I, having the structure

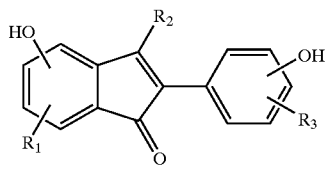

wherein,
R$_1$ is hydrogen, hydroxyl, halogen, trifluoroalkyl of 1–6 carbon atoms, alkyl of 1–6 carbon atoms, cycloalkyl of 3–8 carbon atoms, alkenyl of 2–7 carbon atoms, alkoxy of 1–6 carbon atoms, trifluoroalkoxy of 1–6 carbon atoms, thioalkyl of 1–6 carbon atoms, sulfoxoalkyl of 1–6 carbon atoms, sulfonoalkyl of 1–6 carbon atoms, —CN, —NO$_2$, —CHFCN, —CF$_2$CN, aryl of 6–10 carbon atoms, —NR$_4$R$_5$, —NCOR$_4$, —SR$_4$, —SOR$_4$, —SO$_2$R$_4$, or a 5 or 6-membered heterocyclic ring having 1 to 4 heteroatoms selected from O, N or S; wherein the alkyl or alkenyl moieties are optionally substituted with hydroxyl, —CN, halogen, trifluoroalkyl of 1–6 carbon atoms, trifluoroalkoxy of 1–6 carbon atoms, —COR$_4$, —CO$_2$R$_4$, —CONR$_4$R$_5$, or NR$_4$R$_5$;

R$_2$ is hydrogen, hydroxyl, alkyl of 1–6 carbon atoms, halogen, phenyl substituted with R$_1$, alkylthio of 1–6 carbon atoms, thioalkyl of 1–6 carbon atoms, amino, aminoalkyl of 1–6 carbon atoms, alkylamino of 1–6 carbon atoms, alkoxy of 1–6 carbon atoms, or alkenyl of 2–7 carbon atoms;

R$_3$ is hydrogen, halogen, hydroxyl, alkyl of 1–6 carbon atoms, alkoxy of 1–6 carbon atoms, trifluoroalkyl of 1–6 carbon atoms, or trifluoroalkoxy of 1–6 carbon atoms;

R$_4$ and R$_5$ are each, independently, hydrogen, alkyl of 1–6 carbon atoms, or aryl of 6–10 carbon atoms;

or a pharmaceutically acceptable salt thereof.

10. A method of providing cognition enhancement or neuroprotection; or treating or inhibiting senile dementias, Alzheimer's disease, cognitive decline, stroke, anxiety, or neurodegenerative disorders in a mammal in need thereof, which comprises providing to said mammal an effective amount of a compound of formula I, having the structure

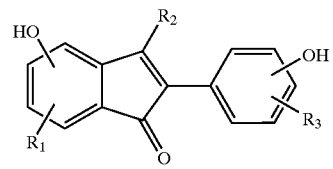

wherein,
R$_1$ is hydrogen, hydroxyl, halogen, trifluoroalkyl of 1–6 carbon atoms, alkyl of 1–6 carbon atoms, cycloalkyl of 3–8 carbon atoms, alkenyl of 2–7 carbon atoms, alkoxy of 1–6 carbon atoms, trifluoroalkoxy of 1–6 carbon atoms, thioalkyl of 1–6 carbon atoms, sulfoxoalkyl of 1–6 carbon atoms, sulfonoalkyl of 1–6 carbon atoms, —CN, —NO$_2$, —CHFCN, —CF$_2$CN, aryl of 6–10 carbon atoms, —NR$_4$R$_5$, —NCOR$_4$, —SR$_4$, —SOR$_4$, —SO$_2$R$_4$, or a 5 or 6-membered heterocyclic ring having 1 to 4 heteroatoms selected from O, N or S; wherein the alkyl or alkenyl moieties are optionally substituted with hydroxyl, —CN, halogen, trifluoroalkyl of 1–6 carbon atoms, trifluoroalkoxy of 1–6 carbon atoms, —COR$_4$, —CO$_2$R$_4$, —CONR$_4$R$_5$, or NR$_4$R$_5$;

R$_2$ is hydrogen, hydroxyl, alkyl of 1–6 carbon atoms, halogen, phenyl substituted with R$_1$, alkylthio of 1–6 carbon atoms, thioalkyl of 1–6 carbon atoms, amino, aminoalkyl of 1–6 carbon atoms, alkylamino of 1–6 carbon atoms, alkoxy of 1–6 carbon atoms, or alkenyl of 2–7 carbon atoms;

R$_3$ is hydrogen, halogen, hydroxyl, alkyl of 1–6 carbon atoms, alkoxy of 1–6 carbon atoms, trifluoroalkyl of 1–6 carbon atoms, or trifluoroalkoxy of 1–6 carbon atoms;

R$_4$ and R$_5$ are each, independently, hydrogen, alkyl of 1–6 carbon atoms, or aryl of 6–10 carbon atoms;

or a pharmaceutically acceptable salt thereof.

11. A method of treating or inhibiting free radical induced disease states in a mammal in need thereof, which comprises providing to said mammal an effective amount of a compound of formula I, having the structure

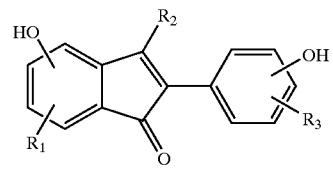

wherein,
R$_1$ is hydrogen, hydroxyl, halogen, trifluoroalkyl of 1–6 carbon atoms, alkyl of 1–6 carbon atoms, cycloalkyl of 3–8 carbon atoms, alkenyl of 2–7 carbon atoms, alkoxy of 1–6 carbon atoms, trifluoroalkoxy of 1–6 carbon atoms, thioalkyl of 1–6 carbon atoms, sulfoxoalkyl of 1–6 carbon atoms, sulfonoalkyl of 1–6 carbon atoms, —CN, —NO₂, —CHFCN, —CF₂CN, aryl of 6–10 carbon atoms, —NR₄R₅, —NCOR₄, —SR₄, —SOR₄, —SO₂R₄, or a 5 or 6-membered heterocyclic ring having 1 to 4 heteroatoms selected from O, N or S; wherein the alkyl or alkenyl moieties are optionally substituted with hydroxyl, —CN, halogen, trifluoroalkyl of 1–6 carbon atoms, trifluoroalkoxy of 1–6 carbon atoms, —COR₄, —CO₂R₄, —CONR₄R₅, or NR₄R₅;

R₂ is hydrogen, hydroxyl, alkyl of 1–6 carbon atoms, halogen, phenyl substituted with R₁, alkylthio of 1–6 carbon atoms, thioalkyl of 1–6 carbon atoms, amino, aminoalkyl of 1–6 carbon atoms, alkylamino of 1–6 carbon atoms, alkoxy of 1–6 carbon atoms, or alkenyl of 2–7 carbon atoms;

R₃ is hydrogen, halogen, hydroxyl, alkyl of 1–6 carbon atoms, alkoxy of 1–6 carbon atoms, trifluoroalkyl of 1–6 carbon atoms, or trifluoroalkoxy of 1–6 carbon atoms;

R₄ and R₅ are each, independently, hydrogen, alkyl of 1–6 carbon atoms, or aryl of 6–10 carbon atoms;

or a pharmaceutically acceptable salt thereof.

12. A method of treating or inhibiting vaginal or vulvar atrophy; atrophic vaginitis; vaginal dryness; pruritus; dyspareunia; dysuria; frequent urination; urinary incontinence; urinary tract infections in a mammal in need thereof, which comprises providing to said mammal an effective amount of a compound of formula I, having the structure

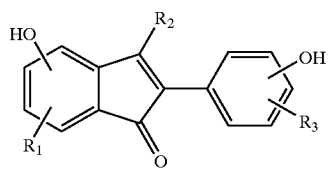

I wherein,

R₁ is hydrogen, hydroxyl, halogen, trifluoroalkyl of 1–6 carbon atoms, alkyl of 1–6 carbon atoms, cycloalkyl of 3–8 carbon atoms, alkenyl of 2–7 carbon atoms, alkoxy of 1–6 carbon atoms, trifluoroalkoxy of 1–6 carbon atoms, thioalkyl of 1–6 carbon atoms, sulfoxoalkyl of 1–6 carbon atoms, sulfonoalkyl of 1–6 carbon atoms, —CN, —NO₂, —CHFCN, —CF₂CN, aryl of 6–10 carbon atoms, —NR₄R₅, —NCOR₄, —SR₄, —SOR₄, —SO₂R₄, or a 5 or 6-membered heterocyclic ring having 1 to 4 heteroatoms selected from O, N or S; wherein the alkyl or alkenyl moieties are optionally substituted with hydroxyl, —CN, halogen, trifluoroalkyl of 1–6 carbon atoms, trifluoroalkoxy of 1–6 carbon atoms, —COR₄, —CO₂R₄, —CONR₄R₅, or NR₄R₅;

R₂ is hydrogen, hydroxyl, alkyl of 1–6 carbon atoms, halogen, phenyl substituted with R₁, alkylthio of 1–6 carbon atoms, thioalkyl of 1–6 carbon atoms, amino, aminoalkyl of 1–6 carbon atoms, alkylamino of 1–6 carbon atoms, alkoxy of 1–6 carbon atoms, or alkenyl of 2–7 carbon atoms;

R₃ is hydrogen, halogen, hydroxyl, alkyl of 1–6 carbon atoms, alkoxy of 1–6 carbon atoms, trifluoroalkyl of 1–6 carbon atoms, or trifluoroalkoxy of 1–6 carbon atoms;

R₄ and R₅ are each, independently, hydrogen, alkyl of 1–6 carbon atoms, or aryl of 6–10 carbon atoms;

or a pharmaceutically acceptable salt thereof.

13. A method of treating or inhibiting vasomotor symptoms in a mammal in need thereof, which comprises providing to said mammal an effective amount of a compound of formula I, having the structure

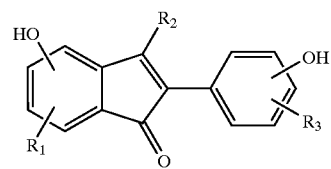

I wherein,

R₁ is hydrogen, hydroxyl, halogen, trifluoroalkyl of 1–6 carbon atoms, alkyl of 1–6 carbon atoms, cycloalkyl of 3–8 carbon atoms, alkenyl of 2–7 carbon atoms, alkoxy of 1–6 carbon atoms, trifluoroalkoxy of 1–6 carbon atoms, thioalkyl of 1–6 carbon atoms, sulfoxoalkyl of 1–6 carbon atoms, sulfonoalkyl of 1–6 carbon atoms, —CN, —NO₂, —CHFCN, —CF₂CN, aryl of 6–10 carbon atoms, —NR₄R₅, —NCOR₄, —SR₄, —SOR₄, —SO₂R₄, or a 5 or 6-membered heterocyclic ring having 1 to 4 heteroatoms selected from O, N or S; wherein the alkyl or alkenyl moieties are optionally substituted with hydroxyl, —CN, halogen, trifluoroalkyl of 1–6 carbon atoms, trifluoroalkoxy of 1–6 carbon atoms, —COR₄, —CO₂R₄, —CONR₄R₅, or NR₄R₅;

R₂ is hydrogen, hydroxyl, alkyl of 1–6 carbon atoms, halogen, phenyl substituted with R₁, alkylthio of 1–6 carbon atoms, thioalkyl of 1–6 carbon atoms, amino, aminoalkyl of 1–6 carbon atoms, alkylamino of 1–6 carbon atoms, alkoxy of 1–6 carbon atoms, or alkenyl of 2–7 carbon atoms;

R₃ is hydrogen, halogen, hydroxyl, alkyl of 1–6 carbon atoms, alkoxy of 1–6 carbon atoms, trifluoroalkyl of 1–6 carbon atoms, or trifluoroalkoxy of 1–6 carbon atoms;

R₄ and R₅ are each, independently, hydrogen, alkyl of 1–6 carbon atoms, or aryl of 6–10 carbon atoms;

or a pharmaceutically acceptable salt thereof.

14. A method of inhibiting conception in a mammal in need thereof, which comprises providing to said mammal an effective amount of a compound of formula I, having the structure

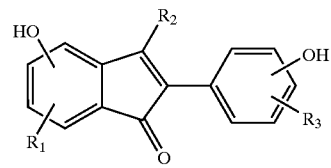

I wherein,

R₁ is hydrogen, hydroxyl, halogen, trifluoroalkyl of 1–6 carbon atoms, alkyl of 1–6 carbon atoms, cycloalkyl of 3–8 carbon atoms, alkenyl of 2–7 carbon atoms, alkoxy of 1–6 carbon atoms, trifluoroalkoxy of 1–6 carbon atoms, thioalkyl of 1–6 carbon atoms, sulfoxoalkyl of 1–6 carbon atoms, sulfonoalkyl of 1–6 carbon atoms, —CN, —NO₂, —CHFCN, —CF₂CN, aryl of 6–10 carbon atoms, —NR₄R₅, —NCOR₄, —SR₄, —SOR₄, —SO₂R₄, or a 5 or 6-membered heterocyclic ring having 1 to 4 heteroatoms selected from O, N or S; wherein the alkyl or alkenyl moieties are optionally substituted with hydroxyl, —CN, halogen, trifluoroalkyl of 1–6 carbon atoms, trifluoroalkoxy of 1–6 carbon atoms, —COR$_4$, —CO$_2$R$_4$, —CONR$_4$R$_5$, or NR$_4$R$_5$;

R$_2$ is hydrogen, hydroxyl, alkyl of 1–6 carbon atoms, halogen, phenyl substituted with R$_1$, alkylthio of 1–6 carbon atoms, thioalkyl of 1–6 carbon atoms, amino, aminoalkyl of 1–6 carbon atoms, alkylamino of 1–6 carbon atoms, alkoxy of 1–6 carbon atoms, or alkenyl of 2–7 carbon atoms;

R$_3$ is hydrogen, halogen, hydroxyl, alkyl of 1–6 carbon atoms, alkoxy of 1–6 carbon atoms, trifluoroalkyl of 1–6 carbon atoms, or trifluoroalkoxy of 1–6 carbon atoms;

R$_4$ and R$_5$ are each, independently, hydrogen, alkyl of 1–6 carbon atoms, or aryl of 6–10 carbon atoms;

or a pharmaceutically acceptable salt thereof.

15. A method of treating or inhibiting arthritis in a mammal in need thereof, which comprises providing to said mammal an effective amount of a compound of formula I, having the structure

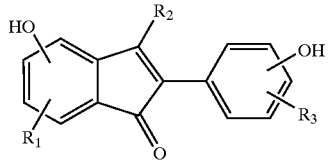

wherein,

R$_1$ is hydrogen, hydroxyl, halogen, trifluoroalkyl of 1–6 carbon atoms, alkyl of 1–6 carbon atoms, cycloalkyl of 3–8 carbon atoms, alkenyl of 2–7 carbon atoms, alkoxy of 1–6 carbon atoms, trifluoroalkoxy of 1–6 carbon atoms, thioalkyl of 1–6 carbon atoms, sulfoxoalkyl of 1–6 carbon atoms, sulfonoalkyl of 1–6 carbon atoms, —CN, —NO$_2$, —CHFCN, —CF$_2$CN, aryl of 6–10 carbon atoms, —NR$_4$R$_5$, —NCOR$_4$, —SR$_4$, —SOR$_4$, —SO$_2$R$_4$, or a 5 or 6-membered heterocyclic ring having 1 to 4 heteroatoms selected from O, N or S; wherein the alkyl or alkenyl moieties are optionally substituted with hydroxyl, —CN, halogen, trifluoroalkyl of 1–6 carbon atoms, trifluoroalkoxy of 1–6 carbon atoms, —COR$_4$, —CO$_2$R$_4$, —CONR$_4$R$_5$, or NR$_4$R$_5$;

R$_2$ is hydrogen, hydroxyl, alkyl of 1–6 carbon atoms, halogen, phenyl substituted with R$_1$, alkylthio of 1–6 carbon atoms, thioalkyl of 1–6 carbon atoms, amino, aminoalkyl of 1–6 carbon atoms, alkylamino of 1–6 carbon atoms, alkoxy of 1–6 carbon atoms, or alkenyl of 2–7 carbon atoms;

R$_3$ is hydrogen, halogen, hydroxyl, alkyl of 1–6 carbon atoms, alkoxy of 1–6 carbon atoms, trifluoroalkyl of 1–6 carbon atoms, or trifluoroalkoxy of 1–6 carbon atoms;

R$_4$ and R$_5$ are each, independently, hydrogen, alkyl of 1–6 carbon atoms, or aryl of 6–10 carbon atoms;

or a pharmaceutically acceptable salt thereof.

16. The method according to claim 15, wherein the arthritis is rheumatoid arthritis, osteoarthritis, or spondyloarthropathies.

17. A method of treating or inhibiting joint swelling or erosion; or treating or inhibiting joint damage secondary to arthroscopic or surgical procedures in a mammal in need thereof, which comprises providing to said mammal an effective amount of a compound of formula I, having the structure

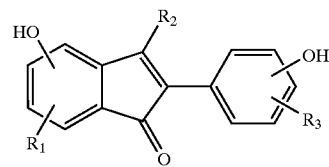

wherein,

R$_1$ is hydrogen, hydroxyl, halogen, trifluoroalkyl of 1–6 carbon atoms, alkyl of 1–6 carbon atoms, cycloalkyl of 3–8 carbon atoms, alkenyl of 2–7 carbon atoms, alkoxy of 1–6 carbon atoms, trifluoroalkoxy of 1–6 carbon atoms, thioalkyl of 1–6 carbon atoms, sulfoxoalkyl of 1–6 carbon atoms, sulfonoalkyl of 1–6 carbon atoms, —CN, —NO$_2$, —CHFCN, —CF$_2$CN, aryl of 6–10 carbon atoms, —NR$_4$R$_5$, —NCOR$_4$, —SR$_4$, —SOR$_4$, —SO$_2$R$_4$, or a 5 or 6-membered heterocyclic ring having 1 to 4 heteroatoms selected from O, N or S; wherein the alkyl or alkenyl moieties are optionally substituted with hydroxyl, —CN, halogen, trifluoroalkyl of 1–6 carbon atoms, trifluoroalkoxy of 1–6 carbon atoms, —COR$_4$, —CO$_2$R$_4$, —CONR$_4$R$_5$, or NR$_4$R$_5$;

R$_2$ is hydrogen, hydroxyl, alkyl of 1–6 carbon atoms, halogen, phenyl substituted with R$_1$, alkylthio of 1–6 carbon atoms, thioalkyl of 1–6 carbon atoms, amino, aminoalkyl of 1–6 carbon atoms, alkylamino of 1–6 carbon atoms, alkoxy of 1–6 carbon atoms, or alkenyl of 2–7 carbon atoms;

R$_3$ is hydrogen, halogen, hydroxyl, alkyl of 1–6 carbon atoms, alkoxy of 1–6 carbon atoms, trifluoroalkyl of 1–6 carbon atoms, or trifluoroalkoxy of 1–6 carbon atoms;

R$_4$ and R$_5$ are each, independently, hydrogen, alkyl of 1–6 carbon atoms, or aryl of 6–10 carbon atoms;

or a pharmaceutically acceptable salt thereof.

18. A method of treating or inhibiting psoriasis or dermatitis in a mammal in need thereof, which comprises providing to said mammal an effective amount of a compound of formula I, having the structure

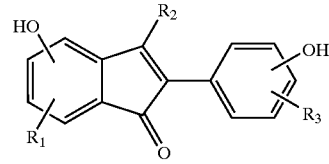

wherein,

R$_1$ is hydrogen, hydroxyl, halogen, trifluoroalkyl of 1–6 carbon atoms, alkyl of 1–6 carbon atoms, cycloalkyl of 3–8 carbon atoms, alkenyl of 2–7 carbon atoms, alkoxy of 1–6 carbon atoms, trifluoroalkoxy of 1–6 carbon atoms, thioalkyl of 1–6 carbon atoms, sulfoxoalkyl of 1–6 carbon atoms, sulfonoalkyl of 1–6 carbon atoms, —CN, —NO$_2$, —CHFCN, —CF$_2$CN, aryl of 6–10 carbon atoms, —NR$_4$R$_5$, —NCOR$_4$, —SR$_4$, —SOR$_4$, —SO$_2$R$_4$, or a 5 or 6-membered heterocyclic ring having 1 to 4 heteroatoms selected from O, N or S; wherein the alkyl or alkenyl moieties are optionally substituted with hydroxyl, —CN, halogen, trifluoroalkyl of 1–6 carbon atoms, trifluoroalkoxy of 1–6 carbon atoms, —COR$_4$, —CO$_2$R$_4$, —CONR$_4$R$_5$, or NR$_4$R$_5$;

R$_2$ is hydrogen, hydroxyl, alkyl of 1–6 carbon atoms, halogen, phenyl substituted with R$_1$, alkylthio of 1–6 carbon atoms, thioalkyl of 1–6 carbon atoms, amino, aminoalkyl of 1–6 carbon atoms, alkylamino of 1–6 carbon atoms, alkoxy of 1–6 carbon atoms, or alkenyl of 2–7 carbon atoms;

R$_3$ is hydrogen, halogen, hydroxyl, alkyl of 1–6 carbon atoms, alkoxy of 1–6 carbon atoms, trifluoroalkyl of 1–6 carbon atoms, or trifluoroalkoxy of 1–6 carbon atoms;

R$_4$ and R$_5$ are each, independently, hydrogen, alkyl of 1–6 carbon atoms, or aryl of 6–10 carbon atoms;

or a pharmaceutically acceptable salt thereof.

19. A method of treating or inhibiting ischemia, reperfusion injury, asthma, pleurisy, multiple sclerosis, systemic lupus erythematosis, uveitis, sepsis, hemmorhagic shock, acular degeneration or type II diabetes in a mammal in need thereof, which comprises providing to said mammal an effective amount of a compound of formula I, having the structure

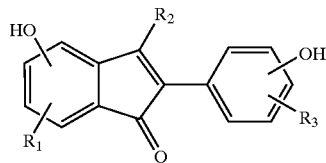

wherein,

R$_1$ is hydrogen, hydroxyl, halogen, trifluoroalkyl of 1–6 carbon atoms, alkyl of 1–6 carbon atoms, cycloalkyl of 3–8 carbon atoms, alkenyl of 2–7 carbon atoms, alkoxy of 1–6 carbon atoms, trifluoroalkoxy of 1–6 carbon atoms, thioalkyl of 1–6 carbon atoms, sulfoxoalkyl of 1–6 carbon atoms, sulfonoalkyl of 1–6 carbon atoms, —CN, —NO$_2$, —CHFCN, —CF$_2$CN, aryl of 6–10 carbon atoms, —NR$_4$R$_5$, —NCOR$_4$, —SR$_4$, —SOR$_4$, —SO$_2$R$_4$, or a 5 or 6-membered heterocyclic ring having 1 to 4 heteroatoms selected from O, N or S; wherein the alkyl or alkenyl moieties are optionally substituted with hydroxyl, —CN, halogen, trifluoroalkyl of 1–6 carbon atoms, trifluoroalkoxy of 1–6 carbon atoms, —COR$_4$, —CO$_2$R$_4$, —CONR$_4$R$_5$, or NR$_4$R$_5$;

R$_2$ is hydrogen, hydroxyl, alkyl of 1–6 carbon atoms, halogen, phenyl substituted with R$_1$, alkylthio of 1–6 carbon atoms, thioalkyl of 1–6 carbon atoms, amino, aminoalkyl of 1–6 carbon atoms, alkylamino of 1–6 carbon atoms, alkoxy of 1–6 carbon atoms, or alkenyl of 2–7 carbon atoms;

R$_3$ is hydrogen, halogen, hydroxyl, alkyl of 1–6 carbon atoms, alkoxy of 1–6 carbon atoms, trifluoroalkyl of 1–6 carbon atoms, or trifluoroalkoxy of 1–6 carbon atoms;

R$_4$ and R$_5$ are each, independently, hydrogen, alkyl of 1–6 carbon atoms, or aryl of 6–10 carbon atoms;

or a pharmaceutically acceptable salt thereof.

20. A method of treating or inhibiting endometriosis in a mammal in need thereof, which comprises providing to said mammal an effective amount of a compound of formula I, having the structure

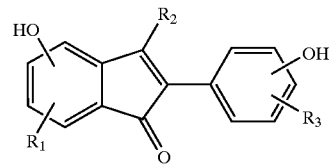

wherein,

R$_1$ is hydrogen, hydroxyl, halogen, trifluoroalkyl of 1–6 carbon atoms, alkyl of 1–6 carbon atoms, cycloalkyl of 3–8 carbon atoms, alkenyl of 2–7 carbon atoms, alkoxy of 1–6 carbon atoms, trifluoroalkoxy of 1–6 carbon atoms, thioalkyl of 1–6 carbon atoms, sulfoxoalkyl of 1–6 carbon atoms, sulfonoalkyl of 1–6 carbon atoms, —CN, —NO$_2$, —CHFCN, —CF$_2$CN, aryl of 6–10 carbon atoms, —NR$_4$R$_5$, —NCOR$_4$, —SR$_4$, —SOR$_4$, —SO$_2$R$_4$, or a 5 or 6-membered heterocyclic ring having 1 to 4 heteroatoms selected from O, N or S; wherein the alkyl or alkenyl moieties are optionally substituted with hydroxyl, —CN, halogen, trifluoroalkyl of 1–6 carbon atoms, trifluoroalkoxy of 1–6 carbon atoms, —COR$_4$, —CO$_2$R$_4$, —CONR$_4$R$_5$, or NR$_4$R$_5$;

R$_2$ is hydrogen, hydroxyl, alkyl of 1–6 carbon atoms, halogen, phenyl substituted with R$_1$, alkylthio of 1–6 carbon atoms, thioalkyl of 1–6 carbon atoms, amino, aminoalkyl of 1–6 carbon atoms, alkylamino of 1–6 carbon atoms, alkoxy of 1–6 carbon atoms, or alkenyl of 2–7 carbon atoms;

R$_3$ is hydrogen, halogen, hydroxyl, alkyl of 1–6 carbon atoms, alkoxy of 1–6 carbon atoms, trifluoroalkyl of 1–6 carbon atoms or trifluoroalkoxy of 1–6 carbon atoms;

R$_4$ and R$_5$ are each, independently, hydrogen, alkyl of 1–6 carbon atoms, or aryl of 6–10 carbon atoms;

or a pharmaceutically acceptable salt thereof.

21. A pharmaceutical composition which comprises a compound of formula I, having the structure

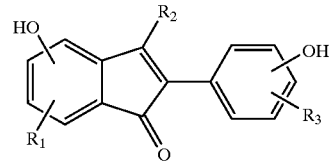

wherein,

R$_1$ is hydrogen, hydroxyl, halogen, trifluoroalkyl of 1–6 carbon atoms, alkyl of 1–6 carbon atoms, cycloalkyl of 3–8 carbon atoms, alkenyl of 2–7 carbon atoms, alkoxy of 1–6 carbon atoms, trifluoroalkoxy of 1–6 carbon atoms, thioalkyl of 1–6 carbon atoms, sulfoxoalkyl of 1–6 carbon atoms, sulfonoalkyl of 1–6 carbon atoms, —CN, —NO$_2$, —CHFCN, —CF$_2$CN, aryl of 6–10 carbon atoms, —NR$_4$R$_5$, —NCOR$_4$, —SR$_4$, —SOR$_4$, —SO$_2$R$_4$, or a 5 or 6-membered heterocyclic ring having 1 to 4 heteroatoms selected from O, N or S; wherein the alkyl or alkenyl moieties are optionally substituted with hydroxyl, —CN, halogen, trifluoroalkyl of 1–6 carbon atoms, trifluoroalkoxy of 1–6 carbon atoms, —COR$_4$, —CO$_2$R$_4$, —CONR$_4$R$_5$, or NR$_4$R$_5$;

$R_2$ is hydrogen, hydroxyl, alkyl of 1–6 carbon atoms, halogen, phenyl substituted with $R_1$, alkylthio of 1–6 carbon atoms, thioalkyl of 1–6 carbon atoms, amino, aminoalkyl of 1–6 carbon atoms, alkylamino of 1–6 carbon atoms, alkoxy of 1–6 carbon atoms, or alkenyl of 2–7 carbon atoms;

$R_3$ is hydrogen, halogen, hydroxyl, alkyl of 1–6 carbon atoms, alkoxy of 1–6 carbon atoms, trifluoroalkyl of 1–6 carbon atoms, or trifluoroalkoxy of 1–6 carbon atoms;

$R_4$ and $R_5$ are each, independently, hydrogen, alkyl of 1–6 carbon atoms, or aryl of 6–10 carbon atoms;

or a pharmaceutically acceptable salt thereof, and a pharmaceutical carrier.

* * * * *

SEQUENCE LISTING

<160> NUMBER OF SEQ ID NOS: 3

<210> SEQ ID NO 1
<211> LENGTH: 19
<212> TYPE: DNA
<213> ORGANISM: artificial sequence
<220> FEATURE:
<223> OTHER INFORMATION: primer

<400> SEQUENCE: 1
cacacggatg gcgcatact                                                19

```
<210> SEQ ID NO 2
<211> LENGTH: 19
<212> TYPE: DNA
<213> ORGANISM: artificial sequence
<220> FEATURE:
<223> OTHER INFORMATION: primer

<400> SEQUENCE: 2
ctcgggatgc accatgaag                                                19

<210> SEQ ID NO 3
<211> LENGTH: 24
<212> TYPE: DNA
<213> ORGANISM: artificial sequence
<220> FEATURE:
<223> OTHER INFORMATION: probe

<400> SEQUENCE: 3
cggcactggt ttccctcaca tgct                                          24
```